(12) United States Patent
Kakei et al.

(10) Patent No.: US 8,792,977 B2
(45) Date of Patent: Jul. 29, 2014

(54) QUANTITATIVE MOTOR FUNCTION EVALUATION SYSTEM

(75) Inventors: Shinji Kakei, Tokyo (JP); Jongho Lee, Tokyo (JP); Yasuhiro Kagamihara, Tokyo (JP)

(73) Assignees: Tokyo Metropolitan Institute of Medical Science, Tokyo (JP); Tokyo Metropolitan Government, Tokyo (JP)

( * ) Notice: Subject to any disclaimer, the term of this patent is extended or adjusted under 35 U.S.C. 154(b) by 1072 days.

(21) Appl. No.: 12/674,709

(22) PCT Filed: Feb. 26, 2008

(86) PCT No.: PCT/JP2008/053735
§ 371 (c)(1),
(2), (4) Date: Feb. 22, 2011

(87) PCT Pub. No.: WO2009/028221
PCT Pub. Date: Mar. 5, 2009

(65) Prior Publication Data
US 2011/0137196 A1 Jun. 9, 2011

(30) Foreign Application Priority Data
Aug. 31, 2007 (JP) ................................. 2007-226596

(51) Int. Cl.
*A61B 5/0488* (2006.01)
*A61B 5/00* (2006.01)
*A61B 5/11* (2006.01)

(52) U.S. Cl.
CPC ............. *A61B 5/0488* (2013.01); *A61B 5/4528* (2013.01); *A61B 5/1124* (2013.01)
USPC .......................................... 600/546; 600/595

(58) Field of Classification Search
USPC ................................................. 600/587, 595
See application file for complete search history.

(56) References Cited

U.S. PATENT DOCUMENTS 5,263,489 A * 11/1993 Johnson et al. ................ 600/546
5,275,174 A * 1/1994 Cook ............................. 600/587
(Continued)

FOREIGN PATENT DOCUMENTS

JP 2000-279463 A 10/2000
JP 2002-514939 A 5/2002
(Continued)

OTHER PUBLICATIONS

Gomi et al. "Equilibrium-Point Control Hypotheses Examined by Measured Arm Stiffness During Multijoint Movement" Science vol. 272, Apr. 5, 1996.*

(Continued)

*Primary Examiner* — Sean Dougherty
*Assistant Examiner* — Michael C Stout
(74) *Attorney, Agent, or Firm* — McDermott Will & Emery LLP

(57) ABSTRACT

The system of the present invention includes (a) means for displaying image information including a target image and a cursor image for tracking the target image; (b) means used when the subject moves the cursor image; (c) means for detecting the state of tracking the target image by the cursor image; (d) means for detecting the muscle active state of the subject using the means (b); (e) means for analyzing the tracking state detected by the means (c) and the muscle active state detected by the means (d); and (f) means for evaluating the motor function of the subject by using results of analysis obtained by the means (e) as indexes.

39 Claims, 16 Drawing Sheets
(14 of 16 Drawing Sheet(s) Filed in Color)

(56) References Cited

U.S. PATENT DOCUMENTS

| | | | |
|---|---|---|---|
| 5,525,061 A * | 6/1996 | Lord | 434/258 |
| 5,562,104 A * | 10/1996 | Hochberg et al. | 600/595 |
| 5,597,373 A * | 1/1997 | Bond et al. | 482/4 |
| 5,695,431 A * | 12/1997 | Bond et al. | 482/1 |
| 5,713,370 A * | 2/1998 | Cook | 600/595 |
| 5,720,711 A * | 2/1998 | Bond et al. | 601/23 |
| 5,772,611 A * | 6/1998 | Hocherman | 600/595 |
| 5,885,231 A * | 3/1999 | Cramer et al. | 600/595 |
| 6,613,000 B1 * | 9/2003 | Reinkensmeyer et al. | 600/587 |
| 6,785,574 B2 * | 8/2004 | Kajitani et al. | 600/546 |
| 7,720,306 B2 * | 5/2010 | Gardiner et al. | 382/276 |
| 7,725,175 B2 * | 5/2010 | Koeneman et al. | 600/546 |
| 2001/0049482 A1 * | 12/2001 | Pozos et al. | 600/587 |
| 2002/0111557 A1 * | 8/2002 | Madill et al. | 600/546 |
| 2002/0191842 A1 * | 12/2002 | Kajitani et al. | 382/159 |
| 2004/0254498 A1 * | 12/2004 | Rahe-Meyer | 600/554 |
| 2005/0187071 A1 * | 8/2005 | Yamashita et al. | 482/1 |
| 2006/0106326 A1 * | 5/2006 | Krebs et al. | 601/40 |
| 2006/0287614 A1 * | 12/2006 | Hogan et al. | 600/595 |
| 2006/0287617 A1 * | 12/2006 | Taub et al. | 601/24 |

FOREIGN PATENT DOCUMENTS

| | | | | |
|---|---|---|---|---|
| JP | 2002-369818 A | | 12/2002 | |
| JP | 2004-016336 A | | 1/2004 | |
| JP | 2005-185557 | * | 7/2005 | A61B 5/0488 |
| JP | 2005-185557 A | | 7/2005 | |
| JP | 3777480 B2 | | 3/2006 | |
| JP | 3785554 B2 | | 3/2006 | |
| JP | 2006247280 A | * | 9/2006 | |
| WO | 96/20643 A1 | | 7/1996 | |

OTHER PUBLICATIONS

C. Harris, et al., Signal-dependent noise determines motor planning, Nature, Aug. 20, 1998, pp. 780-784, vol. 394.

H. Gomi, et al., Equilibrium-Point Control Hypothesis Examined by Measured Arm Stiffness During Multijoint Movement, Science, Apr. 5, 1996, pp. 117-120, vol. 272.

* cited by examiner

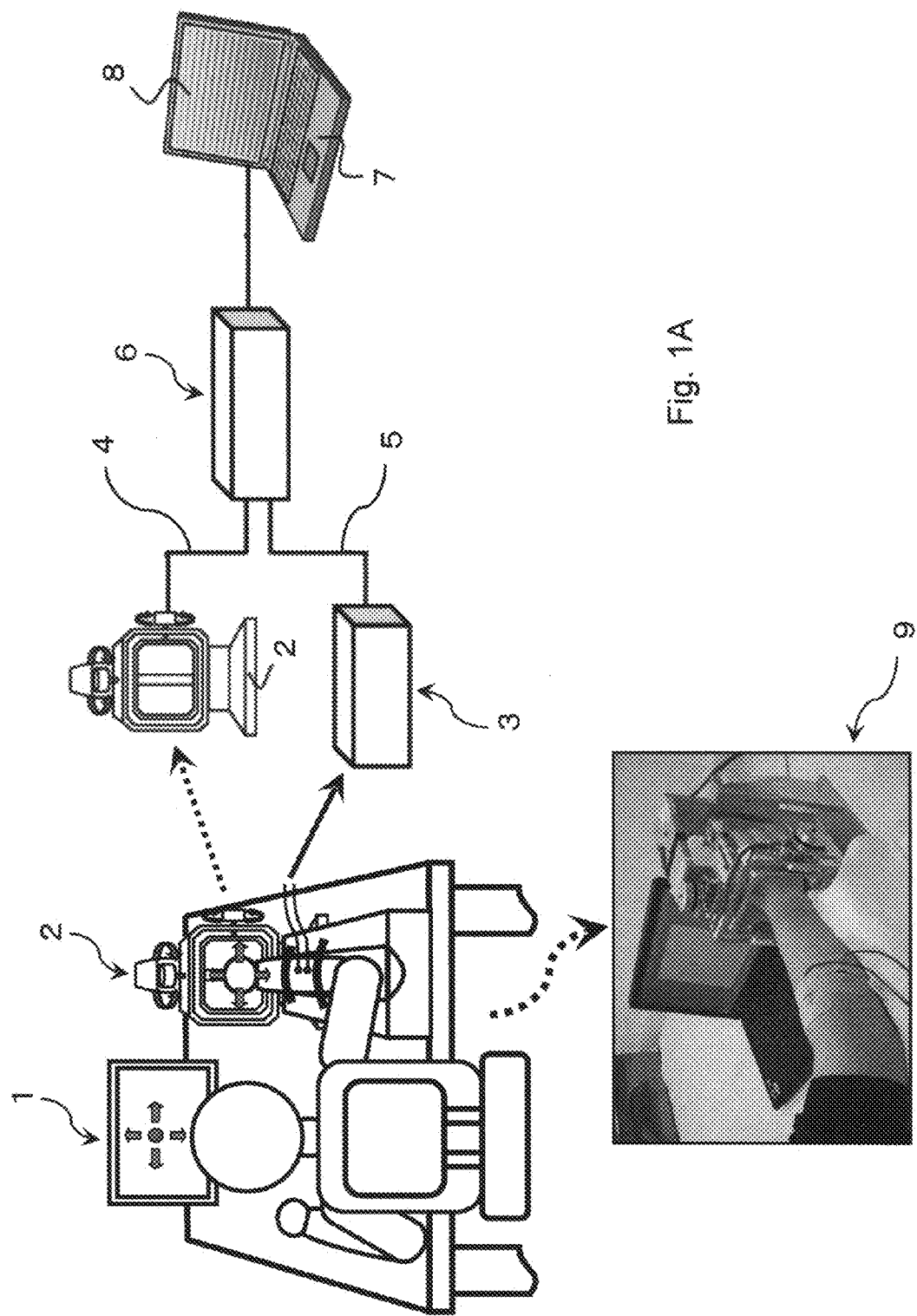

QUANTITATIVE MOTOR FUNCTION EVALUATION SYSTEM

CROSS REFERENCE TO PRIOR APPLICATIONS

This application is a U.S. National Phase application under 35 U.S.C. §371 of International Application No. PCT/JP2008/053735, filed on Feb. 26, 2008 and claims benefit of priority to Japanese Patent Application No. 2007-226596, filed on Aug. 31, 2007. The International Application was published in Japanese on Mar. 5, 2009 as WO 2009/028221 under PCT Article 21(2). All of which are incorporated herein by reference.

TECHNICAL FIELD

The present invention relates to a motor function evaluation system for evaluating the motor function of a subject. In particular, the present invention relates to a motor function evaluation system for quantitatively and objectively evaluating pathological conditions associated with the motor function of a patient with any of various nerve diseases including degenerative diseases of the brain such as Parkinson's disease and cerebellar degenerative disease (specifically, a motor function evaluation system for diagnosis or treatment of the above-described various nerve diseases).

BACKGROUND OF THE INVENTION

Problems of Traditional Neurological Techniques

In order to measure the degree of progression of nerve disease accompanied by motor dysfunction, in particular degenerative disease of the brain and effects of medication and surgery therefor, a qualitative method in which a subject moves following verbal instructions and the movement is observed has been used for over a century. This examination technique has been improved and established over a long period of history, and can be easily practiced anywhere without any particular instrument. However, this technique lacks quantitative characteristics and is influenced by experience and ability of a doctor or the like. Therefore, it is difficult to make a comparison between different subjects or a quantitative and time-dependent comparison between pathological conditions before and after surgery or medication for the same subject.

Demands of the Present Age

There are reasons why the above-described qualitative method has been continuously employed for over a century and objective indexes such as blood sugar level and cholesterol level have not been required. That is, neurological diseases (nerve diseases) such as Parkinson's disease and spinocerebellar degeneration are all intractable diseases, and causes thereof and basic treatment methods therefor have not been elucidated. The traditional technique is enough for making a diagnosis, and when it is diagnosed that a patient has such a disease, to give symptomatic therapy is only one choice. Even if a new diagnosis method is developed with additional costs, it never contributes to the therapy, and therefore, the need thereof was considered to be low.

However, the trend of the times has begun to change dramatically over the past ten years or so. Genes responsible for the above-described intractable diseases have been discovered one after another, and the possibility of basic therapy utilizing stem cell therapy, gene therapy or the like has begun to be eyed. For the purpose of objectively evaluating new treatment methods, the need for objective indexes for abnormal motions is now increasing.

Societal Demand

All neurodegenerative diseases such as Parkinson's disease and its associated diseases and spinocerebellar degeneration are designated as intractable diseases by the national government and local governments, and to these diseases, the public systems for medical cost coverage are applied. Whether or not subsidy for the medical cost is given is a deep problem for patients and their families. At the same time, under the circumstances in which the number of stroke patients is continuously increasing in step with the aging of the population, certification of long-term care need and determination of severity must be suitably made depending on pathological conditions for the purpose of effectively utilizing the limited financial resources. In both the cases, determination should be made fairly and objectively, and for this purpose, it is essential to objectively evaluate motor disorder.

New Trend

With the recent revolutionary development of computer technology, the technical level for quantitatively measuring the motor function has been dramatically increased, and on the other hand, the cost therefor has been dramatically reduced. For example, a CG character can lively move around exactly like a human because a technique called motion capture in which the movement of the entire body of a human is measured and measurements are utilized as digital data was developed. Because of the technical background, an increasing number of attempts to quantitatively describe and evaluate the motor function, in particular the "movement" of a body, have been made. One example thereof is the motor function evaluation system of Murayama et al. (see Japanese Patent Nos. 3777480 and 3785554).

Limit of "Movement"

Essentially, the conventional technique is just description of the "movement". Further, even if the "movement" is recorded, it is not sufficient as an index for the motor function in the case of nerve disease. An abnormal motion appears as abnormality of "movement". However, the same "movement" may occur in response to unlimited different motor commands (i.e., combination of muscle activities). That is, the fundamental problem of ill-posedness is inherent between the "movement" and motor commands. There is a possibility that totally different motor commands (causes) produce the same abnormal motion (result). Therefore, in principle, it is impossible to trace a cause of abnormality in the brain only based on a result of "movement".

SUMMARY OF THE INVENTION

Whatever the current or future basic treatment method for nerve intractable disease is, it acts on the central nervous system, followed by appearance of normalization of motor command. Therefore, regarding the effects of the treatment method, it is necessary to quantitatively, objectively and directly evaluate a motor command itself that is a cause for a "movement", rather than to quantitatively and indirectly evaluate the "movement".

In addition, in order to incorporate such evaluation into daily medical care in a clinical site, it is essential that burden on patients and medical staffs is minimized. That is, means therefor must be noninvasive and simple.

Under such circumstances, the present inventor thought that a problem is to provide a motor function evaluation system for evaluating the motor function of a subject quantitatively, objectively, noninvasively and simply. Further, the present inventor thought that, in order to establish such a system, a problem is to provide a motor function evaluation system, etc. having means for satisfying the following at least 4 specific requirements in a balanced manner: first, major muscle activities of a subject are covered to enable detection of motor commands with sufficient accuracy; second, information of the movement of a subject can also be detected with sufficient accuracy; third, a motor function which is thought to be important for human is targeted for evaluation; and fourth, burden on a subject is minimized. In addition, it was thought that another problem is to provide a motor function evaluation system, etc. for diagnosis or treatment of various nerve diseases including degenerative diseases of the brain such as Parkinson's disease and cerebellar degenerative disease.

The present inventor diligently made researches in order to solve the above-described problems, and successfully expressed the "movement" by replacing it with a simple motor command, which is the activity of only 4 types of muscles (see Example 1). In addition, as means for recording the activities of the 4 types of muscles, a noninvasive technique, a surface electrode was used. As a result, an objective and quantitative motor function evaluation system, in which a motor function which is thought to be important for human is targeted for evaluation, a motor command is detected with sufficient accuracy from the minimum muscle activity of a subject, and at the same time, information of the movement of the subject can also be detected with sufficient accuracy, was realized. In addition, in order to enable noninvasive and simple analysis and evaluation using this system, surrounding elements were organized to construct a system which satisfies all the requirements in a balanced manner. Thus, the present invention was achieved.

Specifically, the present invention is as follows:

(1) A motor function evaluation system for evaluating the motor function of a subject, which includes (a) means for displaying image information including a target image and a cursor image for tracking the target image; (b) means used when the subject moves the cursor image; (c) means for detecting the state of tracking the target image by the cursor image; (d) means for detecting the muscle active state of the subject using the means (b); (e) means for analyzing the tracking state detected by the means (c) and the muscle active state detected by the means (d); and (f) means for evaluating the motor function of the subject by using results of analysis obtained by the means (e) as indexes.

In the system of the present invention, examples of the means (a) include a means having a display screen for displaying the image information.

Examples of the target image include a target image which is at least one selected from the group of (i) an image which moves along a predetermined locus or moves in any direction; (ii) at least two images which are fixed at a predetermined interval; (iii) a line-like image having a predetermined length and width, which is constituted by a straight line and/or a curved line; and (iv) an image only consisting of a starting point and an end point.

Regarding the target image (i), examples of the predetermined locus include a locus which comprises at least one selected from the group consisting of a straight line, a curved line, a circle and a polygon. Further, examples of the target images (i) and (ii) include a target image which comprises at least one shape selected from the group consisting of a circle, an ellipse, a polygon and a star shape. Moreover, examples of the target image (ii) include a target image in which one target image is centered and two or more target images are positioned on a concentric circle of the centered target image.

In the system of the present invention, the means (b) may be provided, for example, separately from the means (a).

Examples of the means (b) include a means which comprises a movable part operated in any direction by a subject and an output part for transmitting, to the means (a), motion information of the movable part as information for moving the cursor image.

Moreover, examples of the means (b) include a means which further has a sensor part for detecting a predetermined parameter regarding motion information of the movable part. In this regard, examples of the predetermined parameter include a parameter which is at least one selected from the group consisting of a position of a portion of the body of a subject involved in operation of the means (b), an angular velocity and a torque.

In the system of the present invention, examples of the means (c) include a means which detects a movement locus of the cursor image as the state of tracking the target image.

In the system of the present invention, examples of the means (d) include a means which detects a myoelectric signal as the muscle active state of a subject. In this regard, the myoelectric signal may be a surface myoelectric signal.

In the system of the present invention, at least one of the means (c) to (f) may be a computer.

Examples of the system of the present invention include a system for evaluating the motor function of the wrist motion of a subject. In this regard, examples of the motor function of the wrist motion include a motor function of a two-degree-of-freedom wrist joint.

In the case where the system of the present invention is for evaluating the motor function of the wrist motion of a subject, examples of the means (b) include a wrist joint manipulandum. Further, examples of the means (d) include a means which detects myoelectric signals of extensor carpi radialis brevis muscle and extensor carpi radialis longus muscle (ECR), extensor carpi ulnaris muscle (ECU), flexor carpi ulnaris muscle (FCU) and flexor carpi radialis muscle (FCR) as the muscle active state of a subject. In this regard, examples of the wrist joint manipulandum include one capable of detecting at least one selected from the group consisting of a position of a wrist joint of a subject, an angular velocity and a torque.

Examples of the system of the present invention include a system used for diagnosis of a nerve disease. In this regard, examples of the diagnosis include evaluation of pathological conditions before and after treatment of a nerve disease. Examples of the treatment of a nerve disease include those utilizing deep brain stimulation therapy, stereotactic neurosurgery, gene therapy, drug therapy or rehabilitation. Further, examples of the nerve disease include a nerve disease accompanied by motor disorder. Specific examples thereof include at least one selected from the group consisting of Parkinson's disease, parkinsonian syndrome, Huntington's disease, athetosis, dystonia, cerebellar and spinal atrophy (including spinocerebellar degeneration), multiple system atrophy, multiple sclerosis, peripheral nerve disease, brain tumor and cerebral stroke.

Examples of the system of the present invention include a system used for treatment of a nerve disease. In this regard, examples of the treatment include rehabilitation of the motor function of a patient with a nerve disease. Examples of the nerve disease include a nerve disease accompanied by motor disorder. Specific examples thereof include at least one selected from the group consisting of Parkinson's disease, parkinsonian syndrome, Huntington's disease, athetosis, dystonia, cerebellar and spinal atrophy (including cerebellar disease and spinocerebellar degeneration), multiple system atrophy, striatonigral degeneration, olivopontocerebellar atrophy, Shy-Drager syndrome, corticobasal degeneration, progressive supranuclear palsy, basal ganglia calcification, parkinsonism-dementia syndrome, diffuse Lewy body disease, Alzheimer's disease, Pick's disease, Wilson's disease, multiple sclerosis, peripheral nerve disease, brain tumor and cerebral stroke. Among them, Parkinson's disease, parkinsonian syndrome, cerebellar and spinal atrophy and cerebral stroke are particularly preferred.

(2) A motor function evaluation method for evaluating the motor function of a subject, which includes the steps of: (a) displaying, on a display means, image information including a target image and a cursor image for tracking the target image; (b) tracking the target image by the cursor image, wherein the subject uses means for moving the cursor image; (c) detecting the state of tracking the target image by the cursor image; (d) detecting the muscle active state of the subject performing the step (b); (e) analyzing the tracking state detected by the step (c) and the muscle active state detected by the step (d); and (f) evaluating the motor function of the subject by using results of analysis obtained by the step (e) as indexes.

Examples of the method of the present invention include a method used for diagnosis of a nerve disease. In this regard, examples of the diagnosis include evaluation of pathological conditions before and after treatment of a nerve disease. Examples of the treatment of a nerve disease include those utilizing deep brain stimulation therapy, stereotactic neurosurgery, gene therapy, drug therapy or rehabilitation. Examples of the nerve disease include a nerve disease accompanied by motor disorder. Specific examples thereof include at least one selected from the group consisting of Parkinson's disease, parkinsonian syndrome, Huntington's disease, athetosis, dystonia, cerebellar and spinal atrophy (including spinocerebellar degeneration), multiple system atrophy, striatonigral degeneration, olivopontocerebellar atrophy, Shy-Drager syndrome, corticobasal degeneration, progressive supranuclear palsy, basal ganglia calcification, parkinsonism-dementia syndrome, diffuse Lewy body disease, Alzheimer's disease, Pick's disease, Wilson's disease, multiple sclerosis, peripheral nerve disease, brain tumor and cerebral stroke.

Examples of the method of the present invention include a method used for treatment of a nerve disease. In this regard, examples of the treatment include rehabilitation of the motor function of a patient with a nerve disease. Examples of the nerve disease include a nerve disease accompanied by motor disorder. Specific examples thereof include at least one selected from the group consisting of Parkinson's disease, parkinsonian syndrome, Huntington's disease, athetosis, dystonia, cerebellar and spinal atrophy (including cerebellar disease and spinocerebellar degeneration), multiple system atrophy, striatonigral degeneration, olivopontocerebellar atrophy, Shy-Drager syndrome, corticobasal degeneration, progressive supranuclear palsy, basal ganglia calcification, parkinsonism-dementia syndrome, diffuse Lewy body disease, Alzheimer's disease, Pick's disease, Wilson's disease, multiple sclerosis, peripheral nerve disease, brain tumor and cerebral stroke. Among them, Parkinson's disease, parkinsonian syndrome, cerebellar and spinal atrophy and cerebral stroke are particularly preferred.

(3) A program used to evaluate the motor function of a subject, which enables a computer to perform the procedures of: (a) displaying, on a display means, image information including a target image and a cursor image for tracking the target image; (b) recording a locus of tracking the target image by the cursor image, wherein the subject uses a means for moving the cursor image; (c) detecting the state of tracking the target image by the cursor image; (d) detecting the muscle active state of the subject who performs tracking of the target image; (e) analyzing the tracking state detected by the procedure (c) and the muscle active state detected by the procedure (d); and (f) evaluating the motor function of the subject by using results of analysis obtained by the analysis in (e) as indexes.

Examples of the program of the present invention include a program used for diagnosis of a nerve disease. In this regard, examples of the diagnosis include evaluation of pathological conditions before and after treatment of a nerve disease. Examples of the treatment of a nerve disease include those utilizing deep brain stimulation therapy, stereotactic neurosurgery, gene therapy, drug therapy or rehabilitation. Further, examples of the nerve disease include a nerve disease accompanied by motor disorder. Specific examples thereof include at least one selected from the group consisting of Parkinson's disease, parkinsonian syndrome, Huntington's disease, athetosis, dystonia, cerebellar and spinal atrophy (including spinocerebellar degeneration), multiple system atrophy, striatonigral degeneration, olivopontocerebellar atrophy, Shy-Drager syndrome, corticobasal degeneration, progressive supranuclear palsy, basal ganglia calcification, parkinsonism-dementia syndrome, diffuse Lewy body disease, Alzheimer's disease, Pick's disease, Wilson's disease, multiple sclerosis, peripheral nerve disease, brain tumor and cerebral stroke.

Examples of the program of the present invention include a program used for treatment of a nerve disease. In this regard, examples of the treatment include rehabilitation of the motor function of a patient with a nerve disease. Examples of the nerve disease include a nerve disease accompanied by motor disorder. Specific examples thereof include at least one selected from the group consisting of Parkinson's disease, parkinsonian syndrome, Huntington's disease, athetosis, dystonia, cerebellar and spinal atrophy (including cerebellar disease and spinocerebellar degeneration), multiple system atrophy, striatonigral degeneration, olivopontocerebellar atrophy, Shy-Drager syndrome, corticobasal degeneration, progressive supranuclear palsy, basal ganglia calcification, parkinsonism-dementia syndrome, diffuse Lewy body disease, Alzheimer's disease, Pick's disease, Wilson's disease, multiple sclerosis, peripheral nerve disease, brain tumor and cerebral stroke. Among them, Parkinson's disease, parkinsonian syndrome, cerebellar and spinal atrophy and cerebral stroke are particularly preferred.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A is a schematic view of a motor function evaluation system.

DETAILED DESCRIPTION OF THE INVENTION

Hereinafter, the present invention will be described in detail. The scope of the present invention is not limited to the description. In addition to the following examples, the present invention can be suitably changed and then practiced within a range in which the effects of the present invention are not reduced.

Note that the entire specification of Japanese Patent Application No. 2007-226596, to which priority is claimed by the present application, is incorporated herein. In addition, all the publications such as prior art documents, laid-open publications, patents and other patent documents cited herein are incorporated herein by reference.

1. Summary of the Present Invention

The present invention relates to a motor function evaluation method for analyzing motor commands of a subject with respect to various motor functions, e.g., motor functions of the wrist motion, and a motor function evaluation system used for practicing the method.

Heretofore, in order to test voluntary motor functions of patients with nerve diseases, qualitative methods such as observation of motions according to verbal instructions have been exclusively employed. Recently, an upper limb motor function evaluation system (for example, see Japanese Laid-Open Patent Publication No. 2004-16336) has been proposed by Murayama, and with respect to evaluation of "movement", quantitative characteristics have been improved. However, in order to more fundamentally evaluate pathological conditions of nerve diseases, it is necessary to directly catch the abnormality of motor commands from the brain, which is the cause of "movement". That is because, due to ill-posedness of motor commands with respect to "movement", it is impossible in principle to specify the abnormality of motor commands based on the abnormality of "movement", and therefore, it is more essential to directly make an evaluation of pathological conditions of nerve diseases at the level of motor commands than to indirectly make the evaluation at the level of "movement". For this reason, the present inventor developed a motor function evaluation system, in which abnormal motions with respect to nerve diseases and the abnormality of motor commands from the brain, which is the cause thereof, can be simultaneously analyzed as muscle activities using the wrist motion.

Figure 1B:
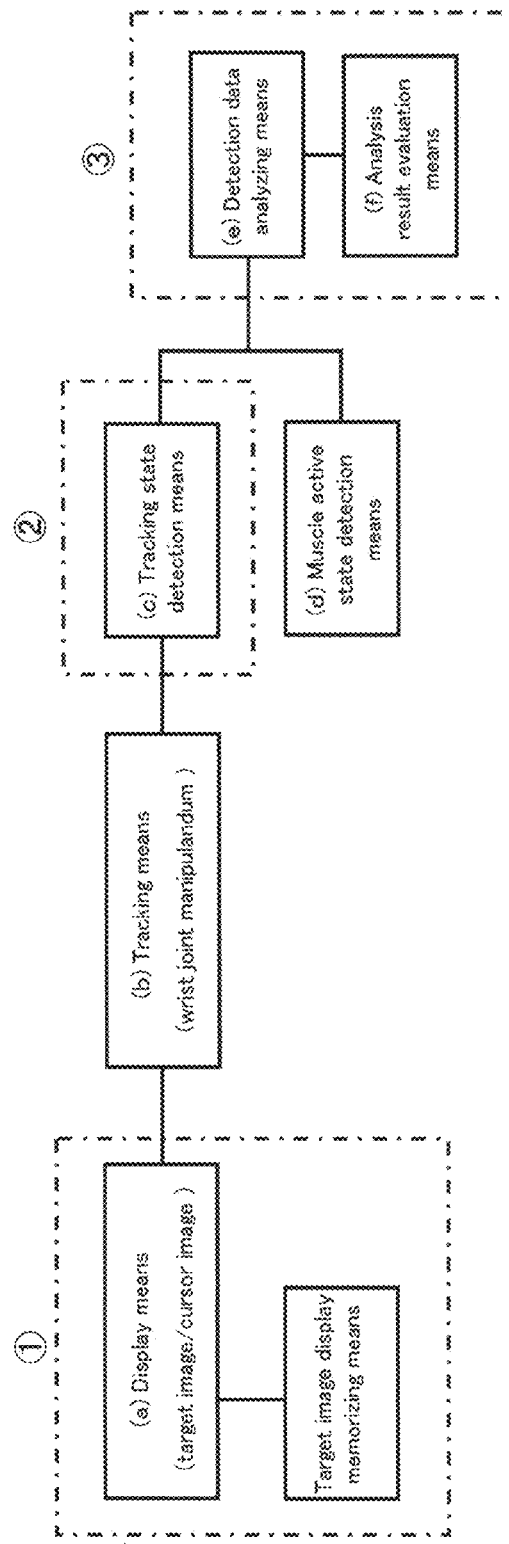
FIG. 1B is a block configuration diagram showing the outline of a motor function evaluation system. In this figure, means (i) to (iii) may be integrated together.

For the purpose of illustration of the motor function evaluation system of the present invention, a schematic view of a motor function evaluation system utilizing the wrist motion is shown in FIG. 1A, and a block configuration diagram of the system is shown in FIG. 1B.

In the motor function evaluation system of the present invention, motor commands regarding various wrist motions of a subject are evaluated as muscle activities. Image information comprising a target image for inducing various wrist motions such as 8-directional motion and number-tracking motion and a cursor image for tracking the target image is displayed on a display means, and based on this image information and using a wrist joint manipulandum, a subject operates the movable part of the manipulandum to move the cursor image. At this time, the movement of a two-degree-of-freedom wrist (X-axis direction and Y-axis direction) is detected as the position of the wrist joint, and the detected data is recorded in an analyzing means such as a computer (for example, at a sampling rate of 2 kHz). In addition, the information of the position of the wrist joint is displayed in real time on a display screen of the display means or a display screen provided to the analyzing means as information of a trajectory (locus) of the cursor image for tracking the target image (i.e., as the state of tracking the target image by the cursor image) and as information of two-degree-of-freedom movement. Meanwhile, the muscle active state of 4 types of muscles related to the wrist motion is detected as a myoelectric signal (electromyographic signal), and the detected data is recorded in an analyzing means such as a computer together with the information of the position of the wrist joint (for example, at a sampling rate of 2 kHz). The data of the position of the wrist joint (data of the state of tracking the target image) and the data of the muscle active state simultaneously recorded in this way are subjected to various analyses such as conversion to muscular tension or joint torque, etc. using a means for data analysis. Thus, in the motor function evaluation system of the present invention, various wrist motions are performed using a wrist joint manipulandum like a mouse, and the correspondence relationship between abnormal motions at that time and the causative abnormality of motor commands can be analyzed.

2. Motor Function Evaluation System

The motor function evaluation system of the present invention (hereinafter sometimes referred to as "the system of the present invention") is for evaluating the motor function of a subject and is an evaluation system having the following means (a) to (f):

(a) means for displaying image information including a target image and a cursor image for tracking the target image (display means);

(b) means used when the subject moves the cursor image (tracking means);

(c) means for detecting the state of tracking the target image by the cursor image (tracking state detection means);

(d) means for detecting the muscle active state of the subject using the means (b) (muscle active state detection means);

(e) means for analyzing the tracking state detected by the means (c) and the muscle active state detected by the means (d) (analyzing means); and (f) means for evaluating the motor function of the subject by using results of analysis obtained by the means (e) as indexes (evaluation means).

The system of the present invention is not limited as long as it can evaluate the motor function of a subject, but is preferably for evaluating the motor function of, in particular, wrist motion, among various motor functions. The motor function of wrist motion to be evaluated is preferably a motor function of a two-degree-of-freedom wrist joint, i.e., a motor function of a wrist joint moving in the horizontal direction (X-axis direction; right/left) and vertical direction (Y-axis direction; up/down) and in a direction of a combination of the aforementioned directions (the same applies to the following).

Hereinafter, the system of the present invention will be described in detail.

Note that with respect to motor functions other than the wrist motor function of a subject, those skilled in the art also can construct and carry out the system of the present invention in consideration of the explanation regarding the motor function of the wrist motion, the common technical knowledge in the technical field, etc.

(1) Display Means

The display means in the system of the present invention is a means for displaying image information including a target image and a cursor image. The display means preferably has a display screen for displaying the image information. Examples of the display screen include full-color or monochrome display type LCD monitors or cathode-ray tube monitors.

The target image means an image to be targeted for tracking by the cursor image, and the shape, size, color tone, movement properties, etc. of the target image are not particularly limited. For example, at least one image selected from the group consisting of images (i) to (iv) below is preferred. Among them, images (i) to (iii) are more preferred.

(i) An image which moves along a predetermined locus or moves in any direction;

(ii) At least two images which are fixed at a predetermined interval;

(iii) A line-like image having a predetermined length and width, which is constituted by a straight line and/or a curved line; and (iv) An image only consisting of a starting point and an end point Examples of the predetermined locus of the image (i) include a locus which has at least one selected from the group of a straight line, a curved line, a circle and a polygon. Regarding the image (i), as the target image which moves along the predetermined locus, for example, an embodiment in which a line representing some sort of a character (number or the like) is used as the predetermined locus and the locus is traced to move the target image is preferred.

As the image (ii) as the target image, for example, an image in which one target image is centered and two or more target images are positioned on a concentric circle of the centered target image is preferred. Specifically, in a preferred embodiment thereof, the centered target image is constantly displayed, whereas the target images on the concentric circle are sequentially displayed one by one, that is, when one of the images is displayed, the other images are not displayed, and when the image which has been displayed becomes hidden, another image among the remaining images is displayed. As an embodiment of such a target image, a target image to be used for evaluation of the function of 8-directional motion is preferred and will be described in the Examples below.

The images (i) and (ii) as the target images preferably include at least one shape selected from the group consisting of, for example, a circle, an ellipse, a polygon and a star shape.

Preferred examples of the image (iii) include a line representing some sort of a character (number or the like) which has a predetermined length and width.

Regarding the image (iv), there is no particular predetermined things except for a starting point and an end point. Therefore, a subject may move the cursor image exactly along an image which the subject thinks (just like tracing an image in the brain).

(2) Tracking Means

The tracking means in the system of the present invention is a means which is used by subjects themselves in order to move the cursor image displayed on the display means. The tracking means may be provided separately from the display means.

Specifically, the tracking means preferably comprises a movable part operated in any direction by a subject and an output part for transmitting, to the display means, motion information of the movable part as information for moving the cursor image. The information transmitted from the output part may be based on analog output or digital output.

It is preferred that the tracking means further comprises a sensor part for detecting a predetermined parameter regarding motion information of the movable part. In this regard, examples of the predetermined parameter include a position of a portion of the body of a subject involved in operation of the tracking means, an angular velocity and a torque.

In the case where the system of the present invention is for evaluating the motor function of the wrist motion of a subject, a wrist joint manipulandum is preferably used as the tracking means. It is preferred that the wrist joint manipulandum can detect a position of a wrist joint of a subject, an angular velocity, a torque, etc. Such a wrist joint manipulandum is commercially available. For example, "Apparatus for measuring 'position, angular velocity and torque' of wrist joint" manufactured by Hoyo Elemec Co., Ltd. or the like may be used.

(3) Tracking State Detection Means

The tracking state detection means in the system of the present invention is a means for detecting the state of tracking the target image by the cursor image which is moved by using the tracking means. The tracking state detected by the means shows the "movement" of a subject, and it is matched to the muscle active state of the subject described below for analysis.

The tracking state to be detected is not limited, but examples thereof include (i) a tracking state represented by a locus (continuous locus) of the movement of the cursor image tracking the target image; and (ii) a tracking state in which the position, moving direction and moving velocity of the cursor image tracking the target image are represented by a vector per unit time. In addition, (iii) a tracking state which represents the movement per se of a part of the body of a subject who uses the tracking means may also be employed. As an example of the tracking state (iii), when the system of the present invention is for evaluating the motor function of the wrist motion, for example, the movement state of the movable part of a wrist joint manipulandum operated by a subject and the movement angle of a wrist joint operating the movable part may be respectively recorded as a horizontal parameter and a vertical parameter.

The tracking state detection means may be a means using a computer. Further, the means may be incorporated into at least one of the other means constituting the system of the present invention, in particular, the display means, analyzing means and evaluation means.

(4) Muscle Active State Detection Means

The muscle active state detection means in the system of the present invention is a means for detecting the muscle active state of a subject using the tracking means (specifically a part of the body of the subject).

As the muscle active state to be detected, a myoelectric signal (electromyographic signal) is preferred. In particular, from the viewpoint of convenience and reduction of burden on a subject, a surface myoelectric signal is more preferred.

Figure 2A:
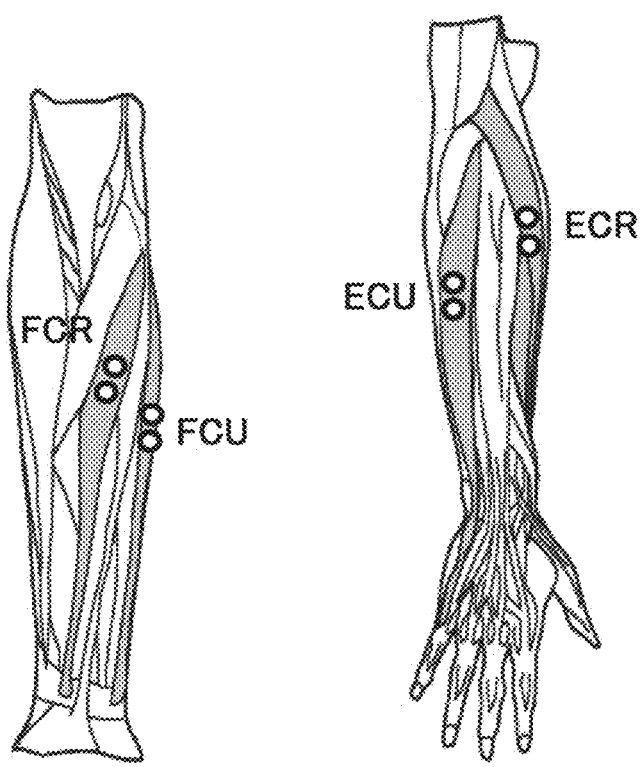
FIG. 2A shows muscles related to the wrist motion. In this figure, ECR represents extensor carpi radialis muscle, ECU represents extensor carpi ulnaris muscle, FCU represents flexor carpi ulnaris muscle, and FCR represents flexor carpi radialis muscle.
Figure 2B:
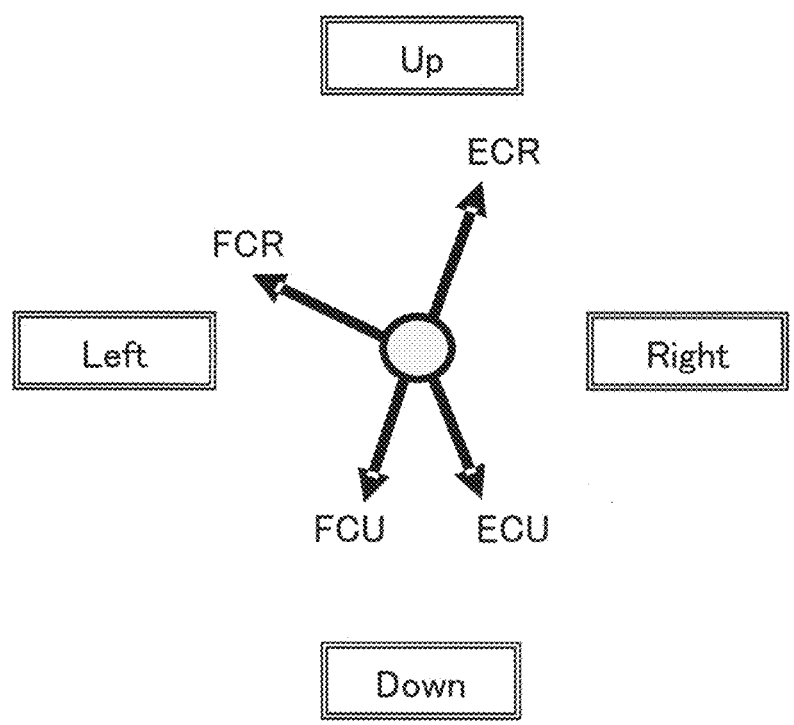
FIG. 2B shows the mechanical action of muscles related to the wrist motion (specifically, the direction of the mechanical action of each muscle).

When detecting the myoelectric signal, usually, such signals of preferably 2 or more, more preferably 3 or more, and still more preferably 4 or more types of muscles involved in use of the tracking means are detected. In the case where the system of the present invention is for evaluating the motor function of the wrist motion of the subject, the detection of myoelectric signal is preferably conducted, for example, with respect to the following 4 types of muscles involved in the wrist motion, among many types of muscles existing in the forearm (in the upper limb, the part from the elbow down): extensor carpi radialis muscle (extensor carpi radialis brevis muscle+extensor carpi radialis longus muscle (ECR)); extensor carpi ulnaris muscle (ECU); flexor carpi ulnaris muscle (FCU); and flexor carpi radialis muscle (FCR) (see FIG. 2A). These 4 types of muscles (ECR, ECU, FCU and FCR) are arranged in the body (forearm of upper limb) so as to cover the movement of two-degree-of-freedom wrist joint in a balanced manner (see FIG. 2B). Therefore, in many types of wrist motions, the correspondence relationship between the "movement" of a subject and the muscle activity (motor command) can be effectively and easily analyzed with high reliability. In this regard, FIG. 2B will be explained below. In FIG. 2B, regarding the arrangement of the direction of the wrist corresponding to the state where a pole set up perpendicularly to the ground (horizontal surface) is gripped by the right hand, the direction of mechanical action given to the wrist joint by each of the muscles (the movement direction of the wrist joint) is shown as an arrow. Specifically, each arrow in FIG. 2B shows the direction of the movement of the wrist joint at the time of artificially providing electrical stimulation to each of the 4 types of muscles based on the actual measurement. For example, it can be understood from FIG. 2B that when stimulating ECR alone, the wrist moves to the upper direction and rather to the right side, and that when stimulating FCU, the wrist moves to the lower direction and rather to the left side. Regarding such a mechanical action of each of the 4 types of muscles, the same action is recognized even when each muscle acts according to the motor command instead of artificial electrical stimulation. Accordingly, for example, when ECR acts during performing a predetermined motor task, ECR pulls the wrist to the upper direction and rather to the right side with a strength proportional to the level of the muscle activity (magnitude of the myoelectric signal). The direction to which the wrist joint moves is determined by the balance of the action of pulling each other (mechanical action) by the 4 types of muscles to the directions indicated by respective arrows (FIG. 2B).

The muscle active state detection means may be a means using a computer. Further, the means may be incorporated into the other means constituting the system of the present invention, in particular, the display means, analyzing means and evaluation means.

(5) Analyzing Means

The analyzing means in the system of the present invention is a means for analyzing the tracking state and the muscle active state which are detected by the above-described detection means. That is, the analyzing means is a means in which the detection data related to the tracking state and the detection data related to the muscle active state are respectively quantified or schematized (including graphing) and the correspondence between the two detection data is analyzed according to need. For example, based on the data obtained by the above-described muscle active state detection means, values of desired parameters can be analyzed. Preferred examples of the parameters include: Variability of Total Contraction (VTC); Directionality of Muscle Activity (DMA); Balance component of Muscle Activity (BMA); and Success Rate of Visually-guided tracking (SRV). Regarding specific definitions of the parameters (methods for calculating values), the below-described description of working examples may be referred to.

Note that the analyzing means may have a means for converting the type of signal of the data obtained by each of the detection means into a desired type, e.g., an A/D interface.

The analyzing means may be a means using a computer. Further, the means may be incorporated into at least one of the other means constituting the system of the present invention, in particular, the display means, tracking state detection means and evaluation means (most preferably evaluation means).

(6) Evaluation Means

The evaluation means in the system of the present invention is a means for evaluating the motor function of a subject using results of analysis obtained by the analyzing means as indexes. The way to evaluate in the evaluation means is not limited as long as results of analysis obtained are used as indexes, but in particular, evaluation in which analysis results of detection data of the muscle active state of a subject are emphasized is preferred. The detection data of the muscle active state may be used as very useful indexes by which the relationship between nerve disease accompanied by motor disorder and abnormal motion can be objectively and quantitatively evaluated, which cannot be fundamentally evaluated only by the detection data of the "movement" of a subject (i.e., the detection data of the tracking state). Specifically, as shown in the working example described below (in particular, FIGS. 11A to 11D), among analysis results related to Variability of Total Contraction (VTC), Directionality of Muscle Activity (DMA), Balance component of Muscle Activity (BMA) and Success Rate of Visually-guided tracking (SRV), 2 or more are preferably combined for evaluation. Examples of the combination include: DMA and SRV; BMA and VTC; BMA, VTC and SRV; and DMA and VTC. Such evaluation of the motor function using the combination of parameters is two-dimensionally or three-dimensionally (or more) plotted based on values of the parameters. By confirming what kind of region (cluster) a subject is included in (belongs to), it can be easily, objectively and quantitatively evaluated which type of nerve disease the subject suffers from or whether or not the subject is a normal (healthy) subject as a control. Therefore, as described later, such evaluation is particularly useful as evaluation in the case where the motor function evaluation system of the present invention is used as a system for diagnosing or treating a nerve disease.

The evaluation means may have a database or the like comprising many analysis results obtained in advance (analysis results of the detection data of the tracking state and the muscle active state). By comparing analysis results obtained with information from such a database, for example, the possibility of a nerve disease accompanied by motor disorder, pathological conditions thereof, etc. can be easily evaluated.

The evaluation means may be a means using a computer. Further, the means may be incorporated into at least one of the other means constituting the system of the present invention, in particular, the display means, tracking state detection means and analyzing means (most preferably analyzing means).

(7) Application of Motor Function Evaluation System

Application of the system of the present invention is not limited, but preferred examples thereof include diagnosis of a nerve disease (or detection of a nerve disease). As the nerve disease, a nerve disease accompanied by motor disorder is preferred. Specific examples thereof include Parkinson's disease, parkinsonian syndrome, Huntington's disease, athetosis, dystonia, cerebellar and spinal atrophy (including cerebellar disease and spinocerebellar degeneration), multiple system atrophy, striatonigral degeneration, olivopontocerebellar atrophy, Shy-Drager syndrome, corticobasal degeneration, progressive supranuclear palsy, basal ganglia calcification, parkinsonism-dementia syndrome, diffuse Lewy body disease, Alzheimer's disease, Pick's disease, Wilson's disease, multiple sclerosis, peripheral nerve disease, brain tumor and cerebral stroke. Among them, Parkinson's disease, parkinsonian syndrome, cerebellar and spinal atrophy, and cerebral stroke are particularly preferred.

In this regard, the above-described diagnosis (or detection) includes judging whether or not a condition is a nerve disease and evaluating time-dependent pathological conditions before and after or during treatment of a nerve disease (i.e., severity of disease condition, degree of change of disease condition, etc.). In this regard, evaluation of time-dependent pathological conditions during treatment includes evaluation for deciding a therapeutic method or strategy in real time during treatment (evaluation for navigation). Examples of the therapy of a nerve disease in which time-dependent pathological conditions before and after or during the therapy are evaluated include deep brain stimulation therapy (DBS), stereotactic neurosurgery, gene therapy, drug therapy and rehabilitation. In particular, in DBS, the optimum stimulation site and stimulus strength can be judged, and in drug therapy (e.g., Menesit), the optimum dosage can be judged.

Further, as the application of the system of the present invention, treatment of a nerve disease is also preferred. As the nerve disease, a nerve disease accompanied by motor disorder is preferred. Specific examples thereof include Parkinson's disease, parkinsonian syndrome, Huntington's disease, athetosis, dystonia, cerebellar and spinal atrophy (including cerebellar disease and spinocerebellar degeneration), multiple system atrophy, striatonigral degeneration, olivopontocerebellar atrophy, Shy-Drager syndrome, corticobasal degeneration, progressive supranuclear palsy, basal ganglia calcification, parkinsonism-dementia syndrome, diffuse Lewy body disease, Alzheimer's disease, Pick's disease, Wilson's disease, multiple sclerosis, peripheral nerve disease, brain tumor and cerebral stroke. Among them, Parkinson's disease, parkinsonian syndrome, cerebellar and spinal atrophy, and cerebral stroke are particularly preferred.

As used herein, the treatment of a nerve disease includes rehabilitation of the motor function of a patient with a nerve disease.

As described above, by using the system of the present invention for diagnosis or treatment of a nerve disease, objective and quantitative motor function evaluation at the motor command level, which was impossible to perform in conventional evaluation only based on the "movement" of a subject, can be performed. Therefore, accuracy, efficiency, etc. of diagnosis or treatment of nerve disease can be dramatically improved, and temporal, physical and economic burden on a subject can be significantly reduced.

Therefore, the motor function evaluation system of the present invention can also be provided as, for example, a system for diagnosis (or detection) of a nerve disease and a system for treatment of a nerve disease. In the system for treatment or diagnosis of a nerve disease, treatment or diagnosis is preferably performed based on evaluation results which are obtained by combination of 2 or more of analysis results related to Variability of Total Contraction (VTC), Directionality of Muscle Activity (DMA), Balance component of Muscle Activity (BMA) and Success Rate of Visually-guided tracking (SRV) as described above. For example, the system may utilize the combination of: DMA and SRV; BMA and VTC; BMA, VTC and SRV; and DMA and VTC. In this regard, examples of the system for diagnosis of a nerve disease include a system for judging time-dependent pathological conditions before and after or during treatment of a nerve disease. In particular, as the system for judging time-dependent pathological conditions during treatment, a system for deciding a therapeutic method or strategy in real time during treatment, a so-called navigation system is also included. In addition, as the system for treatment of a nerve disease, for example, a system for judging the state of recovery of motor function after a specific treatment, a so-called motor function rehabilitation system is also included.

3. Motor Function Evaluation Method

The motor function evaluation method of the present invention (hereinafter sometimes referred to as "the method of the present invention") is a motor function evaluation method for evaluating the motor function of a subject, which has the steps of:

(a) displaying, on a display means, image information including a target image and a cursor image for tracking the target image;

(b) tracking the target image by the cursor image, wherein the subject uses means for moving the cursor image;

(c) detecting the state of tracking the target image by the cursor image;

(d) detecting the muscle active state of the subject performing the step (b);

(e) analyzing the tracking state detected by the step (c) and the muscle active state detected by the step (d); and (f) evaluating the motor function of the subject by using results of analysis obtained by the step (e) as indexes.

The method of the present invention is not limited as long as it is a method for evaluating the motor function of a subject. However, among various types of motor functions, in particular, the motor function of the wrist motion is preferably evaluated in the method. The motor function of the wrist motion to be evaluated is preferably a motor function of a two-degree-of-freedom wrist joint.

The details of the method of the present invention can be well understood and practiced by those skilled in the art with reference to the explanations about the system of the present invention (in particular, the explanations in (1) to (6) of item 2 above). In addition, those skilled in the art can practice the method of the present invention with respect to motor functions other than the wrist motion of a subject in consideration of the explanations about the motor function of the wrist motion and the common technical knowledge in the art.

Application of the method of the present invention is not limited. Preferred examples thereof include diagnosis of a nerve disease (or detection of a nerve disease). That is, the present invention provides a method for diagnosing (or detecting) a nerve disease using the system of the present invention. Specifically, for example, the invention provides a method for evaluating pathological conditions before and after treatment of a nerve disease (i.e., severity of disease condition, degree of change of disease condition, etc.) using the system of the present invention. Further, the present invention can also provide use of the motor function evaluation system of the present invention for diagnosing (or detecting) a nerve disease and the motor function evaluation system for diagnosing (or detecting) a nerve disease.

Moreover, examples of preferred applications of the method of the present invention include treatment of a nerve disease. That is, the present invention provides a method for treating a nerve disease using the system of the present invention. Specifically, for example, the present invention provides a method of rehabilitation of the motor function of a patient with a nerve disease using the system of the present invention. Further, the present invention can also provide use of the motor function evaluation system of the present invention for treating a nerve disease and the motor function evaluation system for treating a nerve disease.

Note that the explanation in (7) of item 2 above can be similarly applied to other specific descriptions related to application of the method of the present invention.

4. Program to be Used for Motor Function Evaluation

In order to perform each step in the above-described motor function evaluation method, a computer program, which enables each of the steps such as the display means, tracking means, tracking state detection means, muscle active state detection means, analyzing means and evaluation means in the aforementioned motor function evaluation system to cooperate with each other to act for performing the steps, is required. The program is, for example, stored in an information storage means (ROM, RAM, etc.) built in or connected to a computer for data analysis and evaluation, and required function or treatment is executed by the program.

Therefore, the present invention also provides a computer program for operating the computer as the motor function evaluation system of the present invention.

Specifically, the program of the present invention is a program used for evaluating the motor function of a subject, which enables a computer to perform the procedures of:

(a) displaying, on a display means, image information including a target image and a cursor image for tracking the target image;

(b) recording a locus of tracking the target image by the cursor image, wherein the subject uses a means for moving the cursor image;

(c) detecting the state of tracking the target image by the cursor image;

(d) detecting the muscle active state of the subject who performs tracking of the target image;

(e) analyzing the tracking state detected by the procedure (c) and the muscle active state detected by the procedure (d); and (f) evaluating the motor function of the subject by using results of analysis obtained by the analysis in (e) as indexes.

The computer program of the present invention may be written using a publicly-known program language which can function on a computer used in the system of the present invention or on a network (the program language is not limited, and examples thereof include Perl, C++, Java and Visual Basic). In order to operate the system of the present invention, in addition to the program of the present invention, programs required for a usual computer network, for example, a well-known operating system (OS), Internet browser program, etc. are also used.

The program of the present invention is not limited as long as it is used for evaluating the motor function of a subject.

Among various types of motor functions, in particular, the motor function of the wrist motion is preferably evaluated using the program. The motor function of wrist motion to be evaluated is preferably a motor function of a two-degree-of-freedom wrist joint.

The details of the program of the present invention can be well understood and practiced by those skilled in the art with reference to the explanations about the system of the present invention (in particular, the explanations in (1) to (6) of item 2 above). In addition, those skilled in the art can design and practice the program of the present invention with respect to motor functions other than the wrist motion of a subject in consideration of the explanations about the motor function of the wrist motion and the common technical knowledge in the art.

Application of the program of the present invention is not limited. Preferred examples thereof include diagnosis of a nerve disease (or detection of a nerve disease) and treatment of a nerve disease. That is, the present invention can also provide a program for diagnosing or detecting a nerve disease. Note that the explanation in (7) of item 2 above can be similarly applied to other specific descriptions related to application of the program of the present invention.

The program of the present invention can be stored in a computer-readable recording medium or a memorizing means which can be connected to a computer. A recording medium or memorizing means for a computer containing the program of the present invention is also included in the present invention. Examples of such recording media and memorizing means include magnetic media (e.g., flexible disks and hard disks), optical media (e.g., CDs and DVDs), and magnetooptic media (e.g., MOs and MDs).

EXAMPLES

Hereafter, the present invention will be specifically described by way of illustrative examples. However, the present invention is not limited only to these examples.

Example 1

Figure 3:
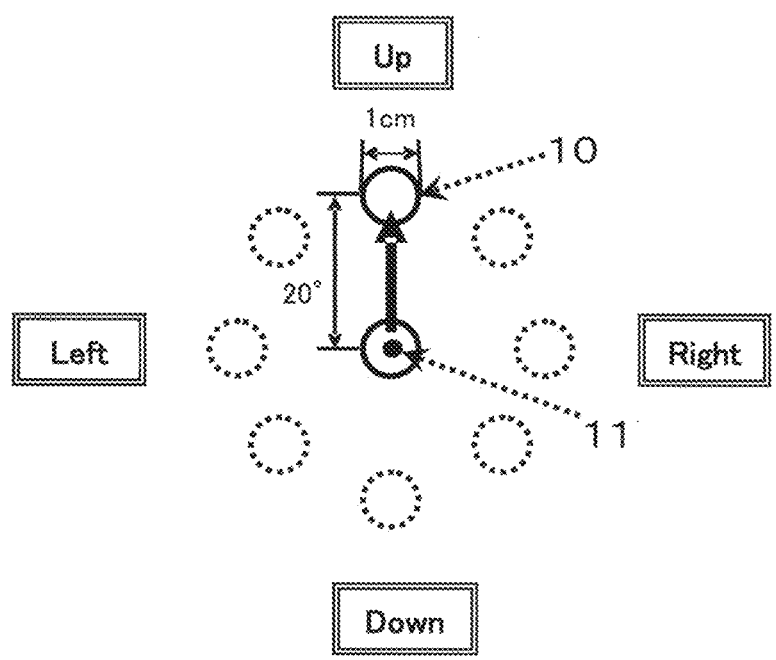
FIG. 3 is a schematic view of 8-directional motion for evaluating the wrist motor function.

In this working example, the 8-directional linear motion of the wrist joint using a wrist joint manipulandum (Step-Tracking Wrist Movement) was employed as a motor task (see FIG. 3).

<Method>

As a motor function evaluation system for the wrist motion, a system similar to the motor function evaluation system shown in FIGS. 1A and 1B was used. As a wrist joint manipulandum, "Apparatus for measuring 'position, angular velocity and torque' of wrist joint" manufactured by Hoyo Elemec Co., Ltd. was used.

Subjects consist of 8 healthy subjects (average age: 51.5) and 8 patients with cerebellar disease (average age: 54.4).

Specifically, as shown in FIG. 3, with respect to the motion in which a cursor image is moved from the central target image to any of 8 surrounding target images (in 8 directions), it was confirmed whether or not the brain sent an appropriate motor command to each muscle in the motion in each direction.

The specific method is described below.

(i) Firstly, when a circular target image having the diameter of 1 cm is displayed on the center of the monitor screen, a subject moves the wrist joint to move the cursor image into the target image and maintains the state.

(ii) Next, on the monitor screen, when a new target image is displayed on a position corresponding to the wrist joint angle of 20°, the subject quickly moves the wrist to move the cursor image into the new target image.

(iii) At this time, the position of the two-degree-of-freedom wrist joint and myoelectric signals of 4 types of agonist muscles (extensor carpi radialis brevis muscle+extensor carpi radialis longus muscle (ECR), extensor carpi ulnaris muscle (ECU), flexor carpi ulnaris muscle (FCU) and flexor carpi radialis muscle (FCR)) associated with the wrist motion are measured and recorded. Note that rough positions of the measured muscles and electrodes are as shown in FIG. 2A. The direction of the mechanical action of each muscle is as shown in FIG. 2B. Regarding the direction of the mechanical action of each muscle, since the 4 types of muscles are arranged so as to cover the movement of two-degree-of-freedom wrist joint in a balanced manner, in many types of wrist motions, the correspondence relationship between the abnormal motion and the causative muscle activity can be analyzed.

<Relationship Between Abnormal Motion and Abnormal Motor Command>

(1) Normalization of Myoelectric Signal

Regarding the measured myoelectric signal, the magnitude of recorded signal varies depending on skin resistance and the position of electrode. Therefore, normalization of myoelectric signal in which the magnitude of myoelectric signal is converted into the value of wrist joint torque was performed. Based on the direction of the mechanical action of each muscle, normalization was performed so that the myoelectric signal in the case where the wrist joint torque at the time of isometric contraction is 1 Nm became 1. In addition, the normalized myoelectric signal was passed through a low-pass filter in order to correct delay of muscle contraction relative to nerve impulse. It is known from neurophysiological study that it is sufficient when the filter is a secondary low-pass filter. In the working examples, a secondary Butterworth filter (cut-off: 4 Hz) was used. In this case, the magnitude of the low-pass-filtered myoelectric signal ($\overline{ECR}$, $\overline{ECU}$, $\overline{FCU}$, $\overline{FCR}$) is approximately proportional to the tension developed in a muscle. Therefore, in the analysis, the filtered myoelectric signal was regarded as a motor command sent from the brain to the muscle.

(2) Identification of Movement of Wrist and Muscle Activity as Motor Command

It was confirmed at the wrist joint torque level to what extent the wrist motion can be explained based on muscle activities of 4 types of muscles associated with the wrist motion ($\overline{ECR}$, $\overline{ECU}$, $\overline{FCU}$, $\overline{FCR}$) (data of myoelectric signal detection). Firstly, using the equation of motion represented by the formula (1) below, the wrist joint torque was obtained from the locus of the wrist motion, and it was examined whether or not the torque can be explained based on the muscle activities of the 4 types of muscles.

$$\vec{\tau}_{kin} = M\ddot{\theta} + B\dot{\theta} + K\theta \tag{1}$$

In this regard, $\vec{\tau}_{kin}$ represents the wrist joint torque obtained from the locus of the wrist motion, and $\theta$, $\dot{\theta}$, and $\ddot{\theta}$ represent the angle of wrist joint, angular velocity and angular acceleration, respectively. In this regard, M is the moment of inertia, and was obtained in a manner in which the hand was regarded as a rigid body. B and K are viscosity coefficient and elastic coefficient, respectively. Based on values which have been reported, in the 8-directional motion, B and K were set as follows: B=0.03 Nms/rad; K=0.2 Nm/rad (note that in the case of number-tracking motion like that of Example 2, B and K were set as follows: B=0.2 Nms/rad; K=0.2 Nm/rad).

With respect to the wrist joint torque obtained from the locus of the wrist motion, the formulae (2-1) and (2-2) below were used, and the linear sum of the myoelectric signals ($\overline{ECR}$, $\overline{ECU}$, $\overline{FCU}$, $\overline{FCR}$) was optimized so that it best corresponds to the wrist joint torque, thereby determining component x ($\vec{\alpha}_{1x\sim4x}$) and component y ($\vec{\alpha}_{1y\sim4y}$) of the action vector (Pulling Vector) of each muscle.

$$\vec{\tau}_x = \overline{ECR} \cdot \vec{\alpha}_{1x} + \overline{ECU} \cdot \vec{\alpha}_{2x} + \overline{FCU} \cdot \vec{\alpha}_{3x} + \overline{FCR} \cdot \vec{\alpha}_{4x} \tag{2-1}$$

$$\vec{\tau}_y = \overline{ECR} \cdot \vec{\alpha}_{1y} + \overline{ECU} \cdot \vec{\alpha}_{2y} + \overline{FCU} \cdot \vec{\alpha}_{3y} + \overline{FCR} \cdot \vec{\alpha}_{4y} \tag{2-2}$$

Figure 4:
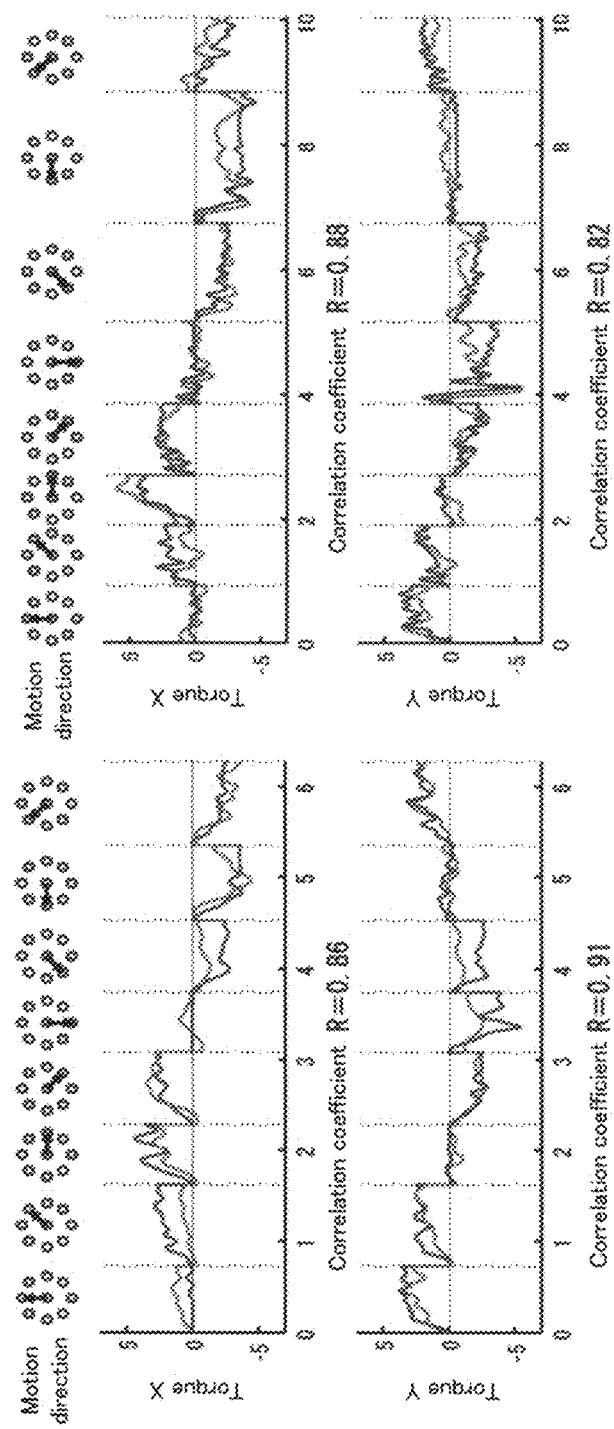
FIG. 4 shows the movement of wrist in 8-directional motion and results of identification of muscle activities as motor commands.

FIG. 4 shows the degree of correspondence between the torque obtained from the movement of the wrist and the torque obtained from the muscle activity in the 8-directional motion. The blue line indicates the torque of wrist obtained from the movement of wrist using the equation of motion, and the red line indicates the linear sum of the 4 types of myoelectric signals. As shown in FIG. 4, it became clear that the torque of wrist is significantly highly correlated with the muscle activities of the 4 types of muscles (correlation coefficient R=0.82 to 0.91) not only in the case of the healthy subject but also in the case of the patient with cerebellar disease.

That is, the result means that information by which the abnormal motion can be well explained is included in the muscle activity patterns of the 4 types of muscles. The motor command can be recorded with satisfactory accuracy utilizing only the muscle activities of the 4 types of muscles, and this was newly found in the development of the motor function evaluation system of the present invention and is a significant practical advantage. There are 24 types of muscles of forearm which may be involved in the wrist motion. If the movement of wrist cannot be explained unless all the activities of the muscles are recorded, in addition to the detection of the surface myoelectric signal as in the case of the system of the present invention, use of needle electrodes accompanied by pain is inevitable. In this case, it takes several hours to just place electrodes while identifying muscles, and therefore, such examination is never practical. It is thought that it is impossible to repeat such examination.

<Analysis Evaluation of Abnormal Motor Function in the Case of Nerve Disease (Cerebellar Disease)>

(1) One Example of Analysis of Abnormal Motor Command: Cerebellar Disease

By using the component x ($\vec{\alpha}_{1x\sim4x}$) and component y ($\vec{\alpha}_{1y\sim4y}$) of the action vector (Pulling Vector) of each muscle in the above-described formulae (2-1) and (2-2) which are determined by optimization, in various wrist motions, the way of contribution of each muscle can be analyzed in detail, and it is possible to infer the central mechanism of abnormal motion in the case of nerve disease. As one example, analysis results of the motor function of the wrist motion of a patient with cerebellar disease (analysis results of motor commands) are shown in FIG. 5.

Figure 5:
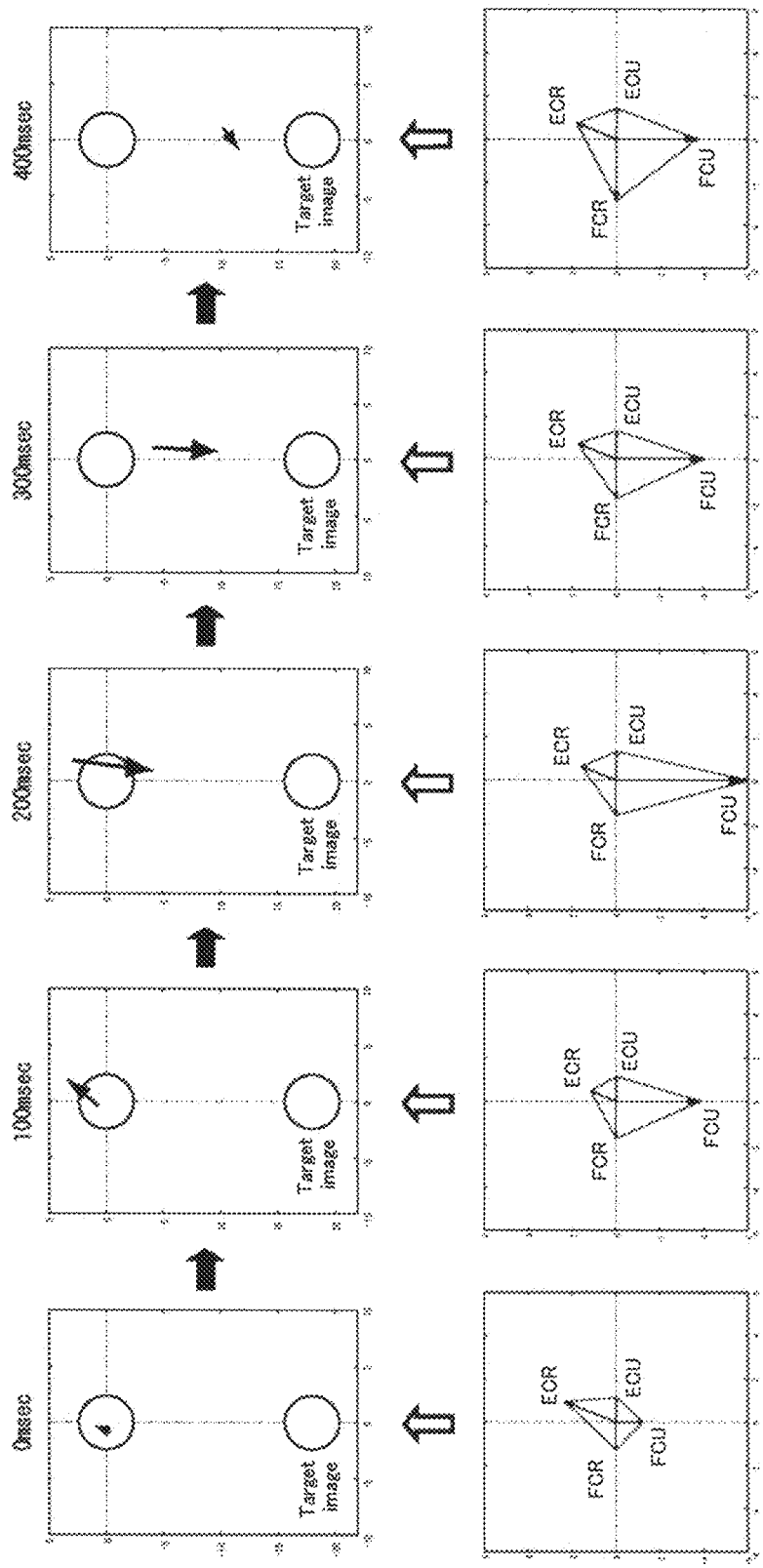
FIG. 5 shows analysis results of motor commands of the patient with cerebellar disease.

In upper figures (5 figures in the upper portion) of FIG. 5, the movement of the wrist joint per 100 msec is represented by a vector. In lower figures (5 figures in the lower portion) of FIG. 5, the degree of contribution of each muscle (ECR, ECU, FCU and FCR) at the moment shown by the corresponding upper figure is shown by the length of an arrow. According to the upper figures of FIG. 5, in the case of the patients with cerebellar disease, for example, abnormal motions, in which the wrist joint moved in the direction opposite to the intended target from the start or stopped on the way and moved to an another direction, occurred. Using the motor function evaluation system of the present invention, as shown in the lower figures of FIG. 5, the motor command causing the wrist motion at each moment was successfully analyzed as the degree of contribution of each muscle. For example, it was found that at the beginning of the motion, an abnormal motor command was sent to ECR which pulls the wrist up and which should be suppressed under normal circumstances and as a result, the wrist moved up. After that, a correct motor command was sent to FCU, resulting in returning to the original downward trajectory. However, after that, an abnormal motor command was sent to FCR, which pulled the wrist to the left. It was clearly recognized that the trajectory was being deviated to the left.

That is, in the conventional motor function evaluation for a patient with nerve disease, only characteristics regarding "movement" as shown in the upper figures of FIG. 5 are extracted and quantified, but by using the motor function evaluation system of the present invention, abnormality of a motor command itself, which causes abnormal motion, can also be analyzed in detail.

The motor function evaluation system of the present invention serves to elucidate the central mechanism of abnormal motion of patients with nerve disease, and at the same time, makes a significantly important contribution to the development of the entirely-new application field, the rehabilitation utilizing motor commands (detection of the muscle active state and analysis results thereof) as indexes.

Example 2

In this working example, the motion of tracking a target image which moves on a predetermined trajectory (Visually-Guided Tracking Movement) using a wrist joint manipulandum was employed as a motor task (see FIG. 6).
<Method>
As a motor function evaluation system for the wrist motion, a system similar to the motor function evaluation system shown in FIGS. 1A and 1B was used. As a wrist joint manipulandum, "Apparatus for measuring 'position, angular velocity and torque' of wrist joint" manufactured by Hoyo Elemec Co., Ltd. was used.

Subjects consist of 10 healthy subjects, 5 patients with cerebellar disease and 13 patients with Parkinson's disease.

Figure 6:
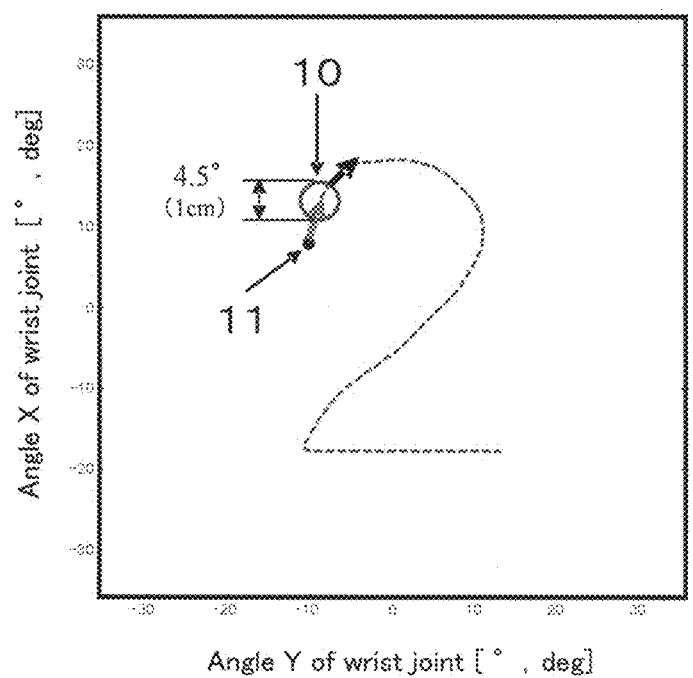
FIG. 6 is a schematic view showing one example of motion to track a moving target image (visual tracking motion) for evaluating the wrist motor function.

As shown in FIG. 6, in the motion of tracking a moving target image, a circular target image having the diameter of 1 cm moves on a trajectory having the shape of number "2" at an almost constant speed, and a subject moves a cursor image shown by a black spot by manipulating the wrist joint manipulandum by the wrist to hold the cursor image in the circular target image.
<Relationship Between Abnormal Motion and Abnormal Motor Command>

Figure 7:
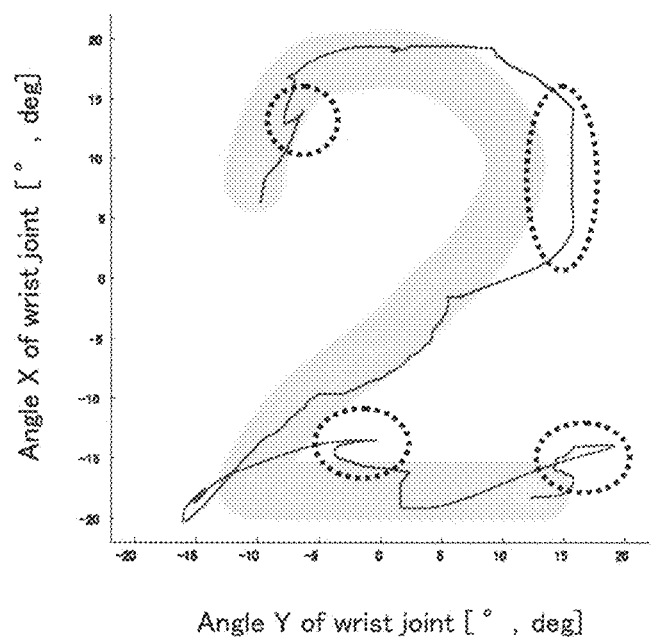
FIG. 7 shows a locus of a cursor image made by a patient with cerebellar disease (results of detection of the state of tracking the target image).

As shown in FIG. 7, a patient with cerebellar disease could not track the moving target image by the cursor image and showed the abnormal motion. In particular, FIG. 7 shows a result in which the trajectory having the shape of number "2" was significantly deviated at 4 portions circled by a dotted line. Note that the motions at the 4 portions time-dependently correspond to 4 positions of dotted lines in the data of the patient with cerebellar disease in the right figure of FIG. 8.

Figure 8:
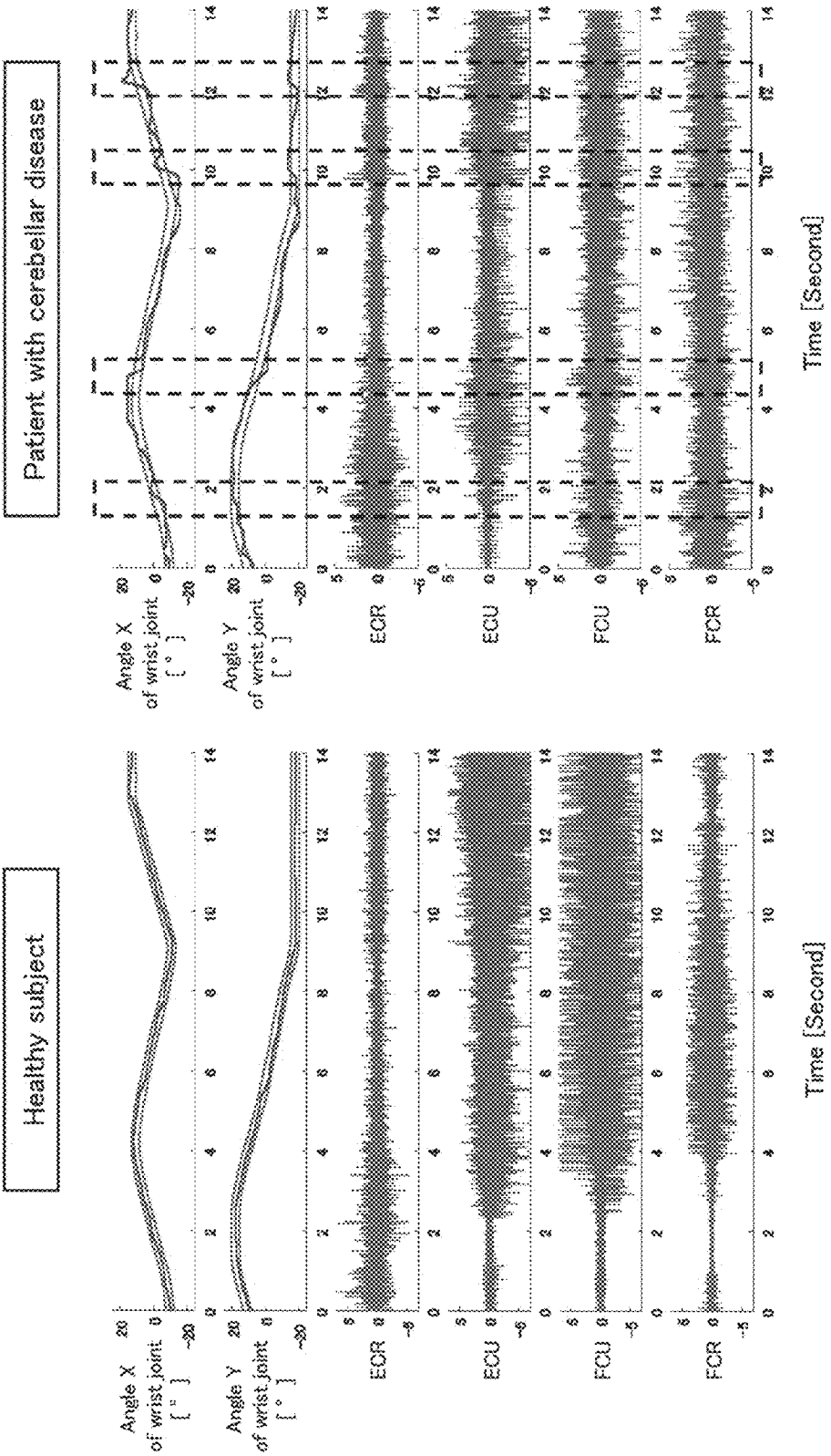
FIG. 8 shows results of detection of the movement of a wrist joint (the state of tracking the target image: upper 2 rows) and results of detection of surface myoelectric signals of 4 types of muscles (the muscle active state: lower 4 rows) regarding a healthy subject and a patient with cerebellar disease.

With respect to the healthy subject and the patient with cerebellar disease, the movement of the wrist joint during the tracking motion (target image tracking state) and surface myoelectric signals of the 4 types o muscles (ECR, ECU, FCU, FCR) (muscle active state) were detected. The results are shown in FIG. 8.

Example 3

Since it was confirmed from the results of Example 1 that information by which the abnormal motion can be well explained is included in the 4 muscle activity patterns associated with the wrist motion, based on the finding thereof, the purpose of this working example was to make positioning (judgment, evaluation, diagnosis) of various nerve diseases such as cerebellar disease and Parkinson's disease at the level of muscle activity and motor command.

Firstly, parameters for the positioning of various nerve diseases (VTC, DMA, BMA, SRV) are shown below.
<Variability of Total Contraction, VTC>

Variability of Total Contraction (VTC) is an average value of the absolute value of the degree of variability of the sum of the magnitude of torque from each muscle ($|\vec{T}_{ECR}|, |\vec{T}_{ECU}|, |\vec{T}_{FCU}|, |\vec{T}_{FCR}|$) shown in FIG. 9, and is defined as the formula (3) below.

$$VTC = \frac{\int \left|\frac{d(|\vec{T}_{ECR}|+|\vec{T}_{ECU}|+|\vec{T}_{FCU}|+|\vec{T}_{FCR}|)}{dt}\right| dt}{t} \quad (3)$$

$$= \frac{\int \left|\frac{d(\overline{ECR}\cdot|\vec{a}_1|+\overline{ECU}\cdot|\vec{a}_2|+\overline{FCU}\cdot|\vec{a}_3|+\overline{FCR}\cdot|\vec{a}_4|)}{dt}\right| dt}{t}$$

In this regard, in formula (3), t is movement time, and $\vec{\alpha}_i$ (i=1-4) is an action vector for converting a pseudo-tension obtained from a surface myoelectric signal into a joint torque (Pulling Vector).

Figure 9:
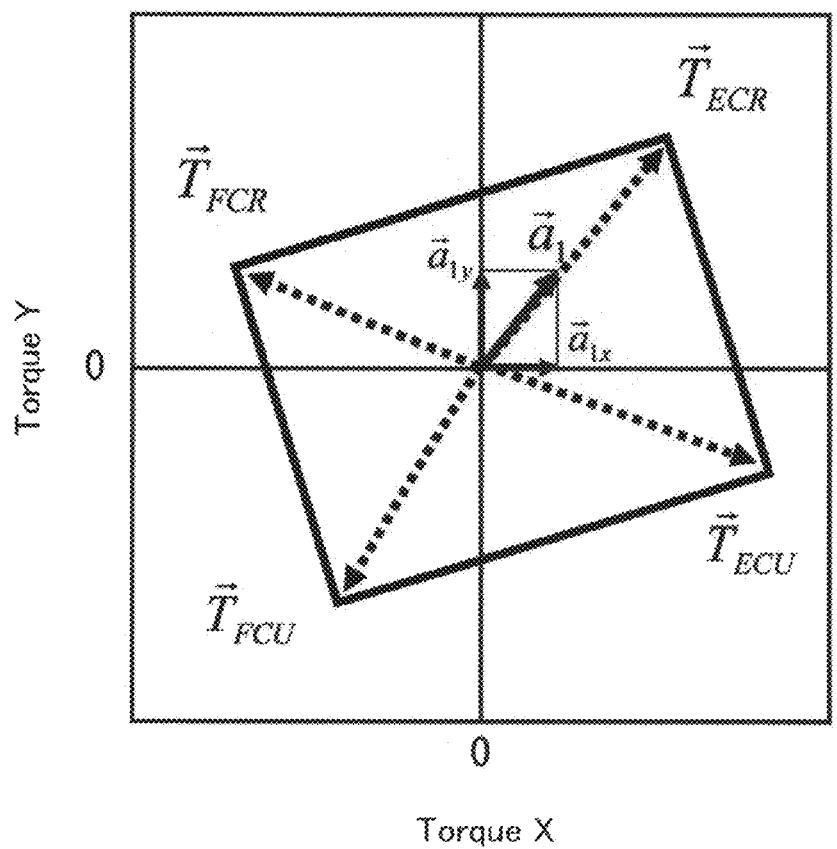
FIG. 9 shows Variability of Total Contraction (VTC).

VTC is constituted by the component x ($\vec{\alpha}_{ix}$) and the component y ($\vec{\alpha}_{iy}$) as shown in FIG. 9, and therefore, the absolute value thereof is defined by formula (4) below:

$$|\vec{\alpha}_i|=\sqrt{(|\vec{\alpha}_{ix}|)^2+(|\vec{\alpha}_{iy}|)^2} \quad (4)$$

Figure 11A:
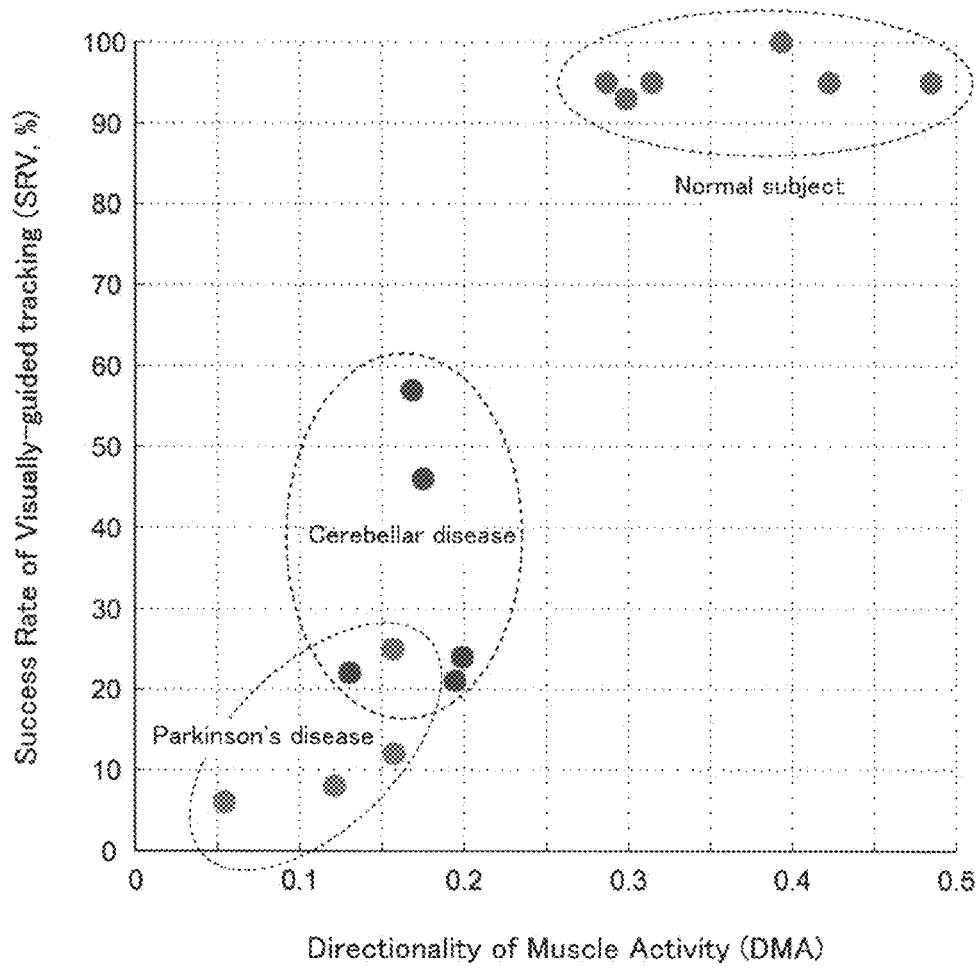
FIG. 11A shows the position of each disease. Specifically, the figure shows the relationship between Directionality of Muscle Activity (DMA) and Success Rate of Visually-guided tracking (SRV).
Figure 11B:
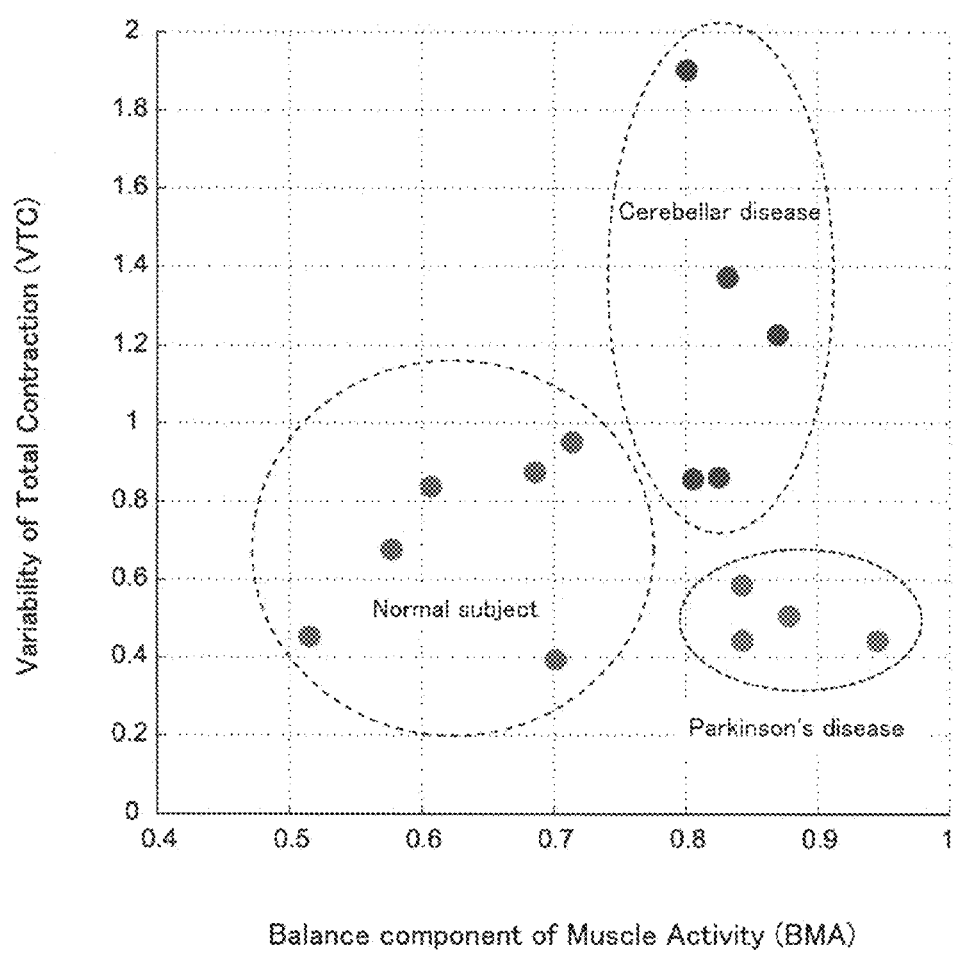
FIG. 11B shows the position of each disease. Specifically, the figure shows the relationship between Balance component of Muscle Activity (BMA) and Variability of Total Contraction (VTC).

From a functional viewpoint, Variability of Total Contraction (VTC) represents the severity of change of the motor command (muscle activity). Therefore, VTC increases when the muscle activity suddenly changes a lot. For example, in the case of motor ataxia due to cerebellar disorder (patient with cerebellar disease), during the motion, activities of the 4 types of muscles continued to suddenly change a lot without regularity, and as a result, VTC was significantly high (FIG. 11B). On the other hand, in the case of Parkinson's disease, all the muscle activities showed little change and became muscle activities without articulation. As a result, VTC was significantly low (FIG. 11B). In the case of the normal (healthy) subject (normal control), when active muscle activity with articulation was shown, VTC became higher, and when the muscle activity very smoothly changed, VTC became lower. It was characterized in that the distribution thereof was wide (FIG. 11B). It should be noted that even in the same subject, VTC varies systematically depending on characteristics of a motor task. For example, VTC becomes higher in the case of a task in which rapid change of the speed often occurs, and becomes lower in the case of smooth motion. Therefore, comparison thereof must be made utilizing the common motor task (trajectory, speed). Regarding a physiologically normal motion, it is known that a margin of error at the time of reaching a goal is decreased by smoothly changing the muscle activity (motor command) (Harris and Wolpert, Nature, vol. 394, pp. 780-784, 1998). From that standpoint, it seems that maintaining gradual change of motor command is optimal. VTC is a parameter which correlates inversely with the smoothness of change of motor command, but evaluation thereof has an important meaning in view of exercise physiology. In addition to VTC, parameters such as dispersion of Variability of Total Contraction, total muscle activity, dispersion of total muscle activity and variability of each muscle are thought to be useful as parameters for expressing wide variation of motor commands because of very high correlativity with VTC.

<Directionality of Muscle Activity (DMA)>

Figure 10:
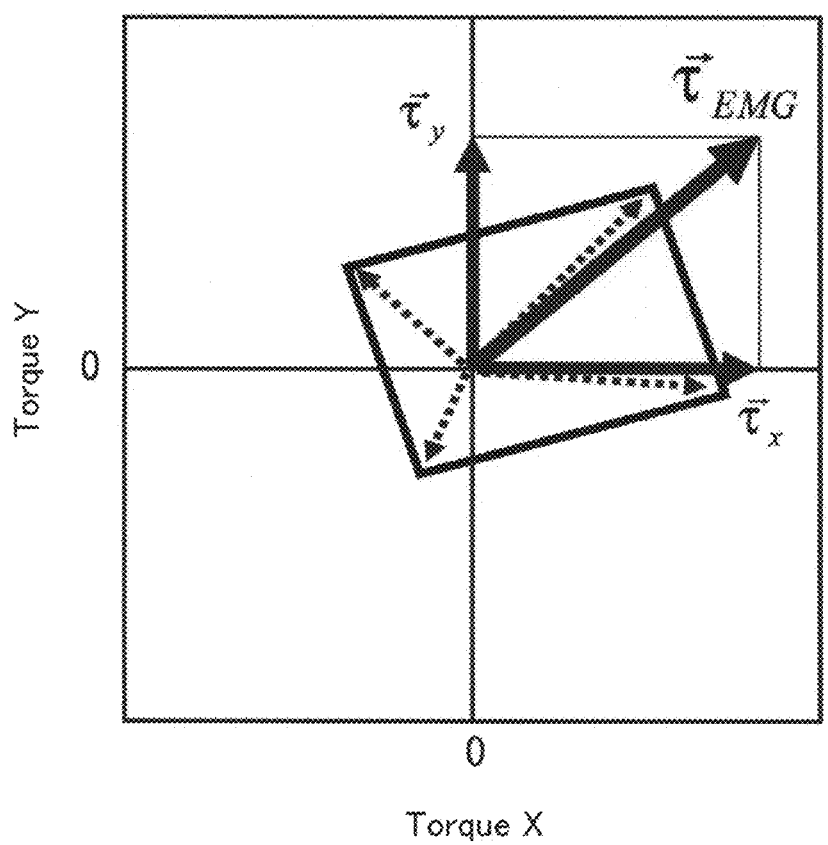
FIG. 10 shows Directionality of Muscle Activity (DMA).

As shown in FIG. 10, Directionality of Muscle Activity (DMA) was evaluated by the ratio between the magnitude of torque of wrist joint obtained from the muscle activity ($|\vec{\tau}_{EMG}|$) and the sum of the magnitude of torque of each muscle ($|\vec{T}_{ECR}|+|\vec{T}_{ECU}|+|\vec{T}_{FCU}|+|\vec{T}_{FCR}|$), and was defined as formula (5) below to be quantified.

$$DMA = \frac{\int \frac{|\vec{\tau}_{EMG}|}{(|\vec{T}_{ECR}|+|\vec{T}_{ECU}|+|\vec{T}_{FCU}|+|\vec{T}_{FCR}|)} dt}{t} \quad (5)$$

In formula (5), as shown in formula (6) below, $\vec{\tau}_{EMG}$ was defined as a torque of wrist joint obtained from 4 myoelectric signals. $\vec{\tau}_{EMG}$ has $\vec{\tau}_x$ and $\vec{\tau}_y$ obtained from formulae (2-1) and (2-2) shown in Example 1 as component x and component y, respectively.

$$\vec{\tau}_{EMG} = \vec{\tau}_x + \vec{\tau}_y \quad (6)$$

Accordingly, the magnitude of $\vec{\tau}_{EMG}$ was obtained using formula (7) below:

$$|\vec{\tau}_{EMG}| = \sqrt{|\vec{\tau}_x|^2 + |\vec{\tau}_y|^2} \quad (7)$$

Directionality of Muscle Activity (DMA) shows the sharpness of directional property of muscle activity, and it became higher in the state in which agonist muscle was selectively activated and antagonist muscle was selectively suppressed, that is, when the contrast between the activity of agonist muscle and that of antagonist muscle was strong. In contrast, DMA became lower when both agonist muscle and antagonist muscle exhibited strong activity and the difference between them was small. For example, when the activities of the 4 muscles were reflected in the torque which moves the wrist to contribute to the movement, DMA became higher, and in contrast, when the activities contributed to stiffness of the joint and postural maintenance as co-contraction, DMA became lower. From the standpoint of energy consumption, when DMA was high, it was in the state in which the muscle activity was efficiently converted into motion energy, and it was thought that the motion was highly efficient. In the case of cerebellar ataxia, it was observed that in order to prevent deviation from a trajectory due to sudden change of muscle activity, the patients maintained the state in which joint stiffness was high by holding high activity of all the muscles (i.e., by straining) before and during motion. For this reason, the denominators under the integral sign of the formula (5) became larger, and as a result, DMA became very small (FIG. 11A). In the case of Parkinson's disease, DMA was also small, but the cause thereof was different from the cause of cerebellar ataxia. In the case of Parkinson's disease, only weak muscle activity was generated in both the agonist muscle and antagonist muscle however hard the patients tried, and therefore, there was little difference between the activity of agonist muscle and that of antagonist muscle. Therefore, the torque, i.e., the numerator under the integral sign of the formula (5) became very small, and as a result, DMA became small. Thus, the causes are totally different from each other, but the two disease groups are in common with each other on the point that motor commands with articulation could not be produced as observed in the case of the normal subjects. Thus, it was found that DMA is a useful parameter which sharply reflects whether or not muscle activity is converted into a torque without loss and intended motion is efficiently performed. Note that DMA becomes the minimum value 0 when the 4 muscle activities are balanced in the resting state (torque 0), and becomes the maximum value 1 when only one muscle is activated and activities of the other muscles are 0 (though it cannot actually happen).

<Balance Component of Muscle Activity (BMA)>

Balance component of Muscle Activity (BMA), which is a parameter paired with the above-described DMA, is also a useful parameter, and is specifically defined as formula (8) below.

$$BMA = \frac{\int \frac{(|\vec{T}_{ECR}|+|\vec{T}_{ECU}|+|\vec{T}_{FCU}|+|\vec{T}_{FCR}|) - |\vec{\tau}_{EMG}|}{(|\vec{T}_{ECR}|+|\vec{T}_{ECU}|+|\vec{T}_{FCU}|+|\vec{T}_{FCR}|)} dt}{t} \quad (8)$$

$$= 1 - \frac{\int \frac{|\vec{\tau}_{EMG}|}{(|\vec{T}_{ECR}|+|\vec{T}_{ECU}|+|\vec{T}_{FCU}|+|\vec{T}_{FCR}|)} dt}{t}$$

$$= 1 - DMA$$

DMA expresses good efficiency of reflection of the muscle activity in the torque. In contrast, BMA is used to evaluate a part of the muscle activity which is consumed for co-contraction and therefore does not appear in the torque. It was thought that this part of the muscle activity is balanced around the wrist and appears as joint tonus, and that it contributes to postural maintenance. BMA becomes the maximum value 1 when the muscle activity is balanced and the torque is 0, and becomes the minimum value 0 when only one muscle is activated and activities of the other muscles are 0 (though it cannot actually happen). As clear from the formula (8), the magnitude of BMA is opposite to the magnitude of DMA. As shown in FIG. 11B, in the case of cerebellar disease and Parkinson's disease, BMA became large because DMA was small, and in the case of the normal subjects, BMA became small because DMA was large.

The concept of joint tonus has played a very important role as a parameter for evaluating the pathological condition of nerve disease in clinical practice. However, the joint tonus used herein is generated by passive motion. Specifically, it was half-quantitatively evaluated as subjective resistance generated when the doctor moved joints in the hands and feet of the patient in the state of relaxation. On the other hand, BMA is a quantitative parameter which reflects a joint tonus during motion, and using the parameter, totally-new information, which had not been successfully obtained in clinical practice, was successfully provided. In addition, when inferring a joint tonus during motion, use of a highly-expensive and large-scale measurement apparatus in a laboratory, long hours of work and a very complicated method (Gomi & Kawato, Science, vol. 272, pp. 117-120, 1996) were required, and therefore such inference was seldom performed. The calculation of BMA in the motor function evaluation system of the present invention established a method for very conveniently inferring a joint tonus during motion. The clinical significance thereof is thought to be noteworthy.

<Success Rate of Visually-Guided Tracking (SRV)>

Though not included in the parameters related to the above-described muscle activities (VTC, DMA, BMA), Success Rate of Visually-guided tracking (SRV) is a parameter for evaluating accuracy of visual tracking motion (see FIG. 6 shown in Example 2), and shows at what percent of the total motion time a cursor can be held in a circular target "○". There tends to be a significant difference between normal subjects and patients with a nerve disease, and the parameter is very useful for evaluation of pathological conditions when combined with characteristics of muscle activities (FIG. 11A and FIG. 11C (described below)). For this reason, SRV was used as an important parameter to be measured in the system of the present invention.

<Position of Cerebellar Disease and Parkinson's Disease from the Standpoint of the Motor Command Level>

Thus, in the system of the present invention, unique and various parameters, which are useful for diagnosis of various nerve diseases and evaluation of pathological conditions thereof, were successfully extracted from the activities of the 4 types of muscles, by which the dynamics of motion can be sufficiently explained. Each of the parameters solely has an inherent functional meaning which characterizes patterns of muscle activities, but it was shown that by combining the parameters for evaluation, the significance and accuracy of the evaluation are further improved.

Figure 11C:
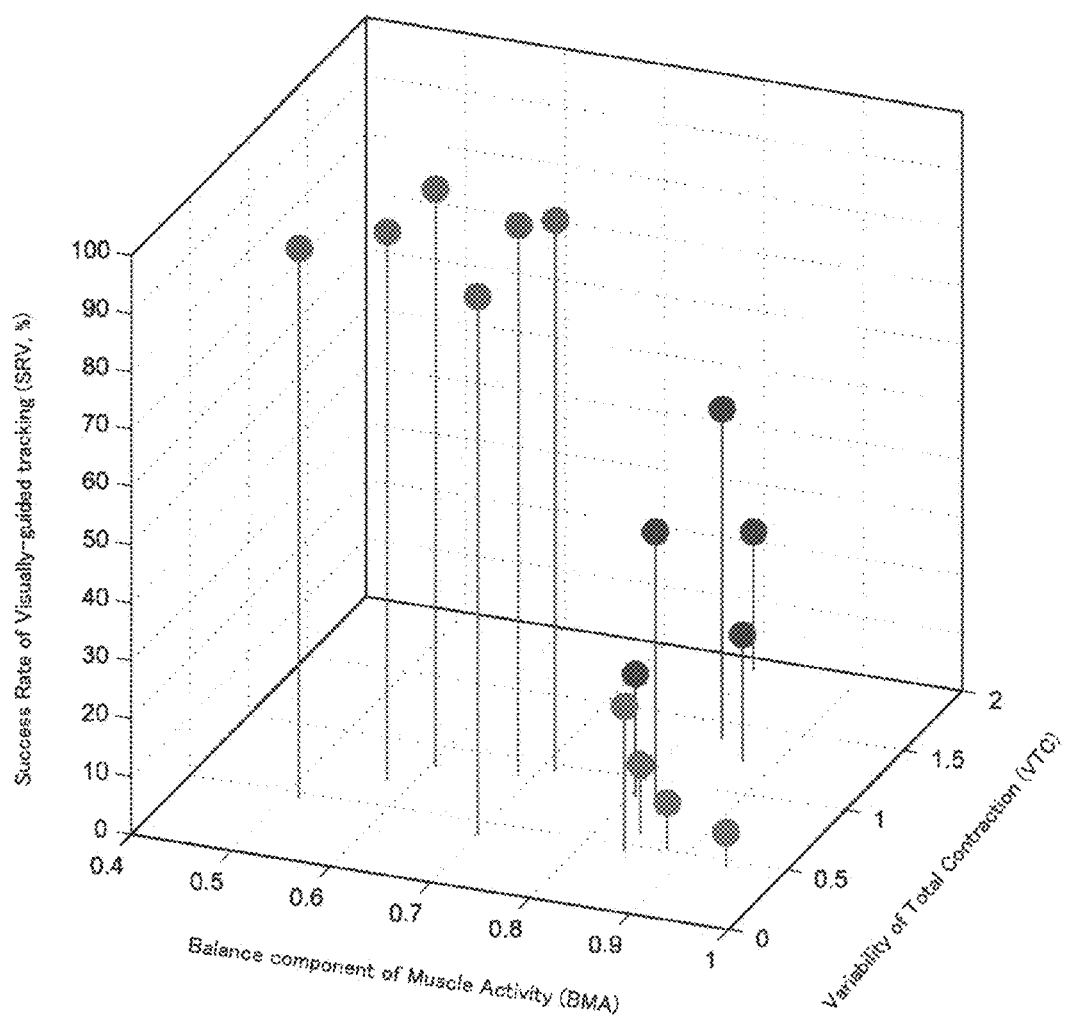
FIG. 11C shows the position of each disease. Specifically, the figure shows the relationship among Balance component of Muscle Activity (BMA), Variability of Total Contraction (VTC) and Success Rate of Visually-guided tracking (SRV).
Figure 11D:
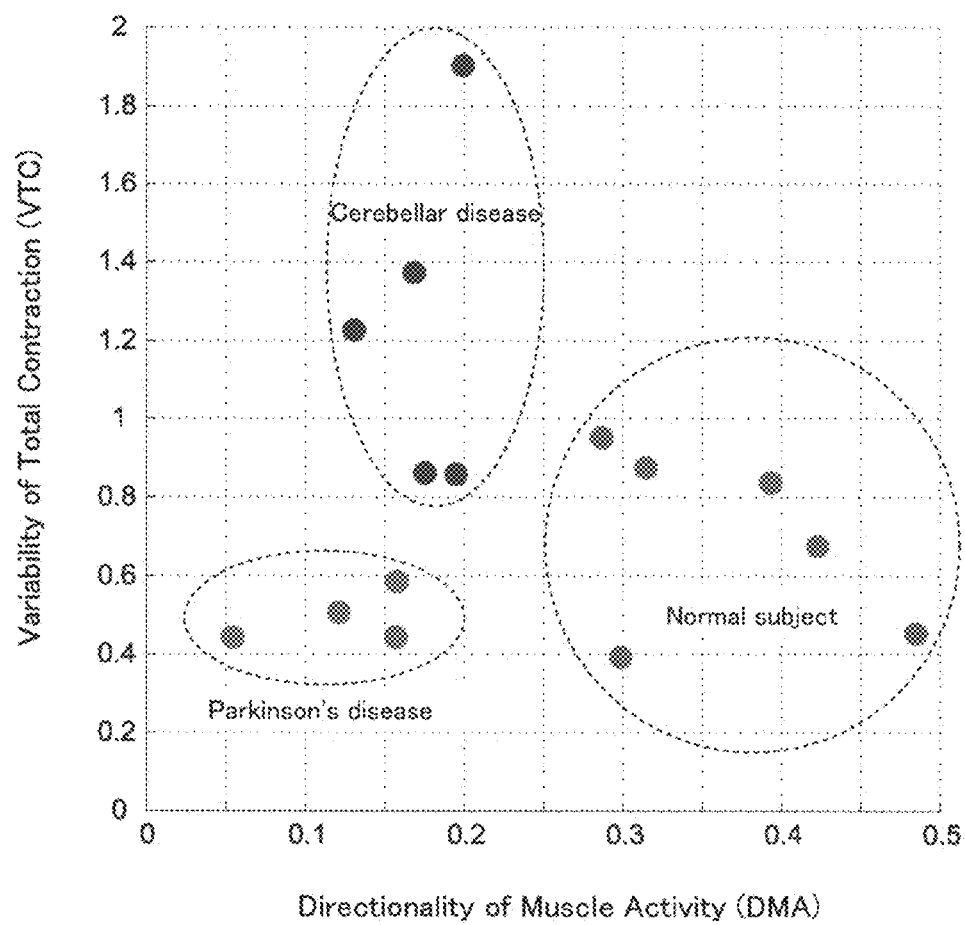
FIG. 11D shows the position of each disease. Specifically, the figure shows the relationship between Variability of Total Contraction (VTC) and Directionality of Muscle Activity (DMA).

For example, when evaluation is made only by Balance component of Muscle Activity, the difference between cerebellar disease and Parkinson's disease is not clear. However, by making evaluation using the combination of Balance component of Muscle Activity and Variability of Total Contraction, the normal subject (normal control), the patient with Parkinson's disease and the patient with cerebellar disease were successfully classified into clearly different clusters (FIG. 11B). Moreover, though the cluster distance between the normal subject (normal control) and the two disease groups (the patient with Parkinson's disease and the patient with cerebellar disease) is seemingly small in FIG. 11B, as shown in FIG. 11C, when making evaluation by further adding an index regarding accuracy of motion (Success Rate of Visually-guided tracking (SRV)), it was successfully clarified that there is a wide gap between the normal subject and the two disease groups. In FIG. 11D, the evaluation results obtained using the combination of Variability of Total Contraction and Directionality of Muscle Activity are shown.

Moreover, based on the relationship related to the cluster position between the normal subject and the respective disease groups, the direction of therapy (therapeutic strategy, therapeutic method) was successfully clarified. Furthermore, it was shown that by evaluation of the degree of approximation to the normal range over time, therapeutic effects can also be evaluated. That is, it was considered that it is possible to construct a navigation system for diagnosis or treatment of nerve diseases by suitably combining the aforementioned various parameters.

According to the present invention, a motor function evaluation system for quantitatively, objectively, noninvasively and simply evaluating the motor function of a subject, for example, the motor function of a two-degree-of-freedom wrist joint, can be provided.

The motor function evaluation system of the present invention is significantly useful on the point that objective and quantitative evaluation results can be obtained in diagnosis (in particular, evaluation of pathological conditions before and after treatment) and treatment (in particular, evaluation of rehabilitation effect on motor function) of nerve diseases such as Parkinson's disease, spinocerebellar degeneration and cerebral stroke. In addition, the motor function evaluation system of the present invention is significantly practical on the point that temporal, physical and economic burden on the above-described patients with nerve disease is small and that the system can be simply used in a clinical site, etc.

The invention claimed is:

1. A motor function evaluation system for evaluating the motor function of a wrist motion of a subject, which comprises:
  a display configured for displaying image information including a target image and a cursor image for tracking the target image;
  a device configured for use by the subject for moving the cursor image by using wrist motion;
  a detector configured for detecting the state of tracking of the target image by the cursor image;
  a sensor configured for detecting myoelectric signals of extensor carpi radialis brevis muscle and extensor carpi radialis longus muscle (ECR), extensor carpi ulnaris muscle (ECU), flexor carpi ulnaris muscle (FCU) and flexor carpi radialis muscle (FCR) as the muscle active state of muscles related to the wrist motion of the subject using the device;
  an analyzer configured for analyzing the tracking state detected by the detector and the muscle active state detected by the sensor; and
  an evaluator configured for evaluating the motor function of the wrist motion of the subject by using results of analysis obtained by the analyzer as indexes.

2. The system according to claim 1, wherein the display comprises a display screen configured for displaying the image information.

3. The system according to claim 1, wherein the target image is at least one selected from the group consisting of:
  (i) an image which moves along a predetermined locus or moves in any direction;
  (ii) at least two images which are fixed at a predetermined interval;
  (iii) a line-like image having a predetermined length and width, which is constituted by a straight line and/or a curved line; and
  (iv) an image only consisting of a starting point and an end point.

4. The system according to claim 3, wherein the predetermined locus comprises at least one selected from the group consisting of a straight line, a curved line, a circle and a polygon.

5. The system according to claim 3, wherein each of the target images (i) and (ii) comprises at least one shape selected from the group consisting of a circle, an ellipse, a polygon and a star shape.

6. The system according to claim 3, wherein in the target image (ii), one target image is centered and two or more target images are positioned on a concentric circle of the centered target image.

7. The system according to claim 1, wherein the device is provided separately from the display.

8. The system according to claim 1, wherein the device comprises a movable part operated in any direction by the subject and an output part for transmitting, to the display, motion information of the movable part as information for moving the cursor image.

9. The system according to claim 8, wherein the device further comprises a sensor part configured for detecting a predetermined parameter regarding motion information of the movable part.

10. The system according to claim 9, wherein the predetermined parameter is at least one selected from the group consisting of a position of a wrist joint of a subject involved in operation of the device, an angular velocity and a torque.

11. The system according to claim 1, wherein the detector is configured for detecting a movement locus of the cursor image as the state of tracking of the target image.

12. The system according to claim 1, wherein the myoelectric signal is a surface myoelectric signal.

13. The system according to claim 1, wherein at least one of the detector, sensor, analyzer and evaluator is a computer.

14. The system according to claim 1, wherein the motor function of the wrist motion is a motor function of a two-degree-of-freedom wrist joint.

15. The system according to claim 1, wherein the device is a wrist joint manipulandum.

16. The system according to claim 15, wherein the wrist joint manipulandum can detect at least one selected from the group consisting of a position of a wrist joint of a subject, an angular velocity and a torque.

17. The system according to claim 10, wherein the evaluator is configured for diagnosis of a nerve disease in the subject by plotting two or more of the predetermined parameters in two or more dimensions, and determining the kind of region or cluster of the plot to which the subject belongs.

18. The system according to claim 17, wherein the evaluator is configured for diagnosis which comprises evaluation of pathological conditions before and after treatment of the nerve disease.

19. The system according to claim 18, wherein the nerve disease is treated utilizing deep brain stimulation therapy, stereotactic neurosurgery, gene therapy or drug therapy.

20. The system according to claim 1, wherein the evaluator is configured for use of the system in treatment of a nerve disease.

21. The system according to claim 20, wherein the treatment comprises rehabilitation of the motor function of a patient with the nerve disease.

22. The system according to claim 17, wherein the nerve disease is a nerve disease accompanied by motor disorder.

23. The system according to claim 22, wherein the nerve disease accompanied by motor disorder is at least one selected from the group consisting of Parkinson's disease, parkinsonian syndrome, Huntington's disease, athetosis, dystonia, cerebellar and spinal atrophy, multiple system atrophy, multiple sclerosis, peripheral nerve disease, brain tumor and cerebral stroke.

24. A motor function evaluation method for evaluating the motor function of a wrist motion of a subject, which comprises the steps of:
displaying, on a display, image information including a target image and a cursor image for tracking the target image;
tracking the target image with the cursor image, wherein the subject uses a device to move the cursor image by using wrist motion;
detecting the state of tracking of the target image by the cursor image;
detecting myoelectric signals of extensor carpi radialis brevis muscle and extensor carpi radialis longus muscle (ECR), extensor carpi ulnaris muscle (ECU), flexor carpi ulnaris muscle (FCU) and flexor carpi radialis muscle (FCR) as the muscle active state of muscles related to the wrist motion of the subject performing the tracking step;
analyzing the tracking state and the muscle active state detected by the steps above; and
evaluating the motor function of the wrist motion of the subject by using results of analysis obtained by the analyzing step as indexes.

25. The method according to claim 24, which comprises diagnosing a nerve disease in the subject, wherein the device used to move the cursor further comprises a sensor part configured for detecting a predetermined parameters selected from the group consisting of a position of a wrist joint of a subject involved in operation of the device, an angular velocity and a torque, and wherein the evaluation comprises plotting the predetermined parameters in two or more dimensions, and determining the kind of region or cluster of the plot to which the subject belongs.

26. The method according to claim 25, wherein the diagnosis comprises evaluation of pathological conditions before and after treatment of the nerve disease.

27. The method according to claim 26, wherein the nerve disease is treated utilizing deep brain stimulation therapy, stereotactic neurosurgery, gene therapy, drug therapy or rehabilitation.

28. The method according to claim 24, wherein the method is used during treatment of a nerve disease.

29. The method according to claim 28, wherein the treatment comprises rehabilitation of the motor function of a patient with the nerve disease.

30. The method according to claim 25, wherein the nerve disease is a nerve disease accompanied by motor disorder.

31. The method according to claim 30, wherein the nerve disease accompanied by motor disorder is at least one selected from the group consisting of Parkinson's disease, parkinsonian syndrome, Huntington's disease, athetosis, dystonia, cerebellar and spinal atrophy, multiple system atrophy, striatonigral degeneration, olivopontocerebellar atrophy, Shy-Drager syndrome, corticobasal degeneration, progressive supranuclear palsy, basal ganglia calcification, parkinsonism-dementia syndrome, diffuse Lewy body disease, Alzheimer's disease, Pick's disease, Wilson's disease, multiple sclerosis, peripheral nerve disease, brain tumor and cerebral stroke.

32. A non-transitory computer-readable recording medium containing a program used to evaluate the motor function of a wrist motion of a subject, wherein the program enables a computer to perform the procedures of:
displaying, on a display, image information including a target image and a cursor image for tracking the target image;
recording a locus of tracking of the target image by the cursor image, wherein the subject uses a device for moving the cursor image by using wrist motion;
detecting the state of tracking of the target image by the cursor image;
detecting myoelectric signals of extensor carpi radialis brevis muscle and extensor carpi radialis longus muscle (ECR), extensor carpi ulnaris muscle (ECU), flexor carpi ulnaris muscle (FCU) and flexor carpi radialis muscle (FCR) as the muscle active state of muscles related to the wrist motion of the subject who performs tracking of the target image;
analyzing the tracking state and the muscle active state detected by the above procedures; and evaluating the motor function of the wrist motion of the subject by using results of analysis obtained by the analysis above as indexes.

33. The recording medium according to claim 32, wherein the device used to move the cursor further comprises a sensor part configured for detecting a predetermined parameters selected from the group consisting of a position of a wrist joint of a subject involved in operation of the device, an angular velocity and a torque, and wherein the program enables evaluation comprising plotting the parameters in two or more dimensions, and determining the kind of region or cluster of the plot to which the subject belongs, which evaluation is used for diagnosis of a nerve disease in the subject.

34. The recording medium according to claim 33, wherein the diagnosis comprises evaluation of pathological conditions before and after treatment of a nerve disease.

35. The recording medium according to claim 34, wherein the nerve disease is treated utilizing deep brain stimulation therapy, stereotactic neurosurgery, gene therapy, drug therapy or rehabilitation.

36. The recording medium according to claim 32, wherein the program enables evaluation for use during treatment of a nerve disease.

37. The recording medium according to claim 36, wherein the treatment comprises rehabilitation of the motor function of a patient with the nerve disease.

38. The recording medium according to claim 33, wherein the nerve disease is a nerve disease accompanied by motor disorder.

39. The recording medium according to claim 38, wherein the nerve disease accompanied by motor disorder is at least one selected from the group consisting of Parkinson's disease, parkinsonian syndrome, Huntington's disease, athetosis, dystonia, cerebellar and spinal atrophy, multiple system atrophy, striatonigral degeneration, olivopontocerebellar atrophy, Shy-Drager syndrome, corticobasal degeneration, progressive supranuclear palsy, basal ganglia calcification, parkinsonism-dementia syndrome, diffuse Lewy body disease, Alzheimer's disease, Pick's disease, Wilson's disease, multiple sclerosis, peripheral nerve disease, brain tumor and cerebral stroke.

* * * * *